(12) United States Patent
Nelson et al.

(10) Patent No.: US 9,782,176 B2
(45) Date of Patent: Oct. 10, 2017

(54) COLLAPSIBLE ANVIL HEAD AND STAPLING APPARATUS

(71) Applicant: Ohio State Innovation Foundation, Columbus, OH (US)

(72) Inventors: Mark Tyler Nelson, Columbus, OH (US); Nathaniel Hogrebe, Columbus, OH (US); Christopher Gordon Scheitlin, Columbus, OH (US); Xiaoli Liu, Columbus, OH (US); Joshua Hoffman, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 806 days.

(21) Appl. No.: 14/079,189

(22) Filed: Nov. 13, 2013

(65) Prior Publication Data

US 2014/0131420 A1   May 15, 2014

Related U.S. Application Data

(60) Provisional application No. 61/725,850, filed on Nov. 13, 2012.

(51) Int. Cl.
*A61B 17/068* (2006.01)
*A61B 17/115* (2006.01)
*A61B 17/11* (2006.01)
*A61B 17/00* (2006.01)

(52) U.S. Cl.
CPC ....... *A61B 17/1155* (2013.01); *A61B 17/1114* (2013.01); *A61B 2017/00818* (2013.01)

(58) Field of Classification Search
CPC .................. A61B 2017/07257; A61B 17/1155

USPC .......................................................... 227/179.1
See application file for complete search history.

(56) References Cited

U.S. PATENT DOCUMENTS

| | | | | |
|---|---|---|---|---|
| 5,839,639 A * | 11/1998 | Sauer | ................ | A61B 17/115 227/153 |
| 6,957,758 B2 * | 10/2005 | Aranyi | ................ | A61B 17/072 227/176.1 |
| 7,516,877 B2 * | 4/2009 | Aranyi | ................ | A61B 17/072 227/176.1 |
| 8,496,157 B2 * | 7/2013 | Olson | ................ | A61B 17/1155 227/176.1 |
| 8,978,955 B2 * | 3/2015 | Aronhalt | ............ | A61B 17/1155 227/175.1 |
| 9,033,204 B2 * | 5/2015 | Shelton, IV | ....... | A61B 17/1155 227/179.1 |

(Continued)

*Primary Examiner* — Andrew M Tecco
(74) *Attorney, Agent, or Firm* — Meunier Carlin & Curfman LLC

(57) ABSTRACT

Various implementations of the invention provide for a one-piece surgical stapling apparatus that includes a stapler head and an anvil head assembly. The anvil head assembly is tiltable between a tilted position and a transverse position, and anvil plates of the anvil head assembly are moveable about one or more hinges between a closed and an open position. When in the tilted and closed positions, the anvil assembly has a reduced footprint that allows the anvil assembly to be passed directly through a trocar and holes created in the bodily tissues, which eliminates the need for separate placement of the anvil head. At the site of the anastomosis, the anvil head assembly can be moved to the transverse and open positions, and the stapling head may be engaged to fire staples against the anvil head.

16 Claims, 28 Drawing Sheets

(56) References Cited

U.S. PATENT DOCUMENTS

| | | | |
|---|---|---|---|
| 9,113,883 B2* | 8/2015 | Aronhalt | A61B 17/1155 |
| 9,125,654 B2* | 9/2015 | Aronhalt | A61B 17/1155 |
| 2006/0201989 A1* | 9/2006 | Ojeda | A61B 17/11 227/175.1 |
| 2012/0234890 A1* | 9/2012 | Aronhalt | A61B 17/1155 227/175.1 |
| 2013/0175315 A1* | 7/2013 | Milliman | A61B 17/1155 227/175.1 |

* cited by examiner

COLLAPSIBLE ANVIL HEAD AND STAPLING APPARATUS

This application claims priority to U.S. Patent Application Ser. No. 61/725,850 filed on Nov. 13, 2012, which is herein incorporated by reference in its entirety.

BACKGROUND

In a laparoscopic roux-en-y gastric bypass procedure, a small stomach pouch is created from the stomach. FIG. 1 illustrates a schematic view of the completed bypass. The small intestine is cut into two pieces 100a, 100b. The portion 100b of the small intestine below the cut line is connected to the newly created small stomach pouch 110 to form the route through which food will pass. The portion 100a of the small intestine above the cut line is reconnected to the small intestine 100c further down the gastrointestinal tract from the newly created small stomach pouch 110. This connection allows for the transport of the bile and pancreatic fluid need for digestion to the gastrointestinal tract. The newly routed small intestine forms a "Y" shape, thus giving the procedure its name.

A circular stapler is used to form an anastomosis between the newly created stomach pouch and the portion of the small intestine below the cut line and between the small intestine and the portion of the small intestine above the cut line. Current circular staplers include a stapler head and a separate anvil head that are inserted through two different holes in the body. For example, the stapler head may be inserted through a trocar in the small intestines, and the anvil head may be passed down the esophagus or placed through a gastrotomy and subsequently encapsulated in the newly created stomach pouch, such as shown in FIGS. 2A and 2B. The stapler head and the anvil head are brought together and connected adjacent the site of the anastomosis. However, aligning the stapler head and the anvil head is time consuming and presents additional risks to the patient. Specifically, if passed down the esophagus, the procedure can result in esophageal or hypopharyngeal injury. If placed through a gastrotomy, the procedure can result in an enlarged trocar site and requires an additional opening and closing of a stomach hole. FIG. 3 illustrates a typical two-piece stapler that has been brought together with the stapler head to complete the anastomosis procedure.

Thus, there is a need in the art for an improved circular stapler that improves the anastomosis procedure by reducing the length, difficulty, and risks associated with the procedure.

BRIEF SUMMARY

A surgical stapling apparatus according to various implementations includes a handle, a surgical staple dispensing head disposed adjacent a distal end of the handle, and an anvil assembly disposed adjacent a distal end of the surgical staple dispensing head. The anvil assembly includes at least two anvil plates that are separately formed from each other, a plunger that has a proximal end, a distal end, and a central portion there between, and a central anvil member. The plunger includes a plunger head at the distal end of the plunger. The plunger is translatable along a y-axis, which extends from a proximal end of the handle to a distal end of the anvil assembly. A portion of the central portion of the plunger extends through the surgical staple dispensing head. The central anvil member includes a hinge connector portion that is pivotably connected to the plunger head at a first point and connected to a fixed hinge at a second point. The fixed hinge is separate from the plunger head, and the first point is offset from the y-axis and the second point is along the y-axis. The central anvil member is configured to rotate about the second point between a tilted position and a transverse position, wherein in the tilted position, a distal surface of the central anvil member is not parallel to a transverse plane extending perpendicularly to the y-axis and, in the transverse position, the distal surface of the central anvil member is substantially parallel to the transverse plane.

The anvil assembly may also include a cable that extends between the anvil plates and the central anvil member. The cable is configured for urging the anvil plates between a closed position and an open position. In the open position, the anvil plates are disposed substantially within the transverse plane. In the closed position, the anvil plates are substantially parallel to the transverse plane. In addition, the plunger is translatable downwardly along the y-axis to urge the central anvil member to rotate about the second point toward the transverse position and is translatable upwardly along the y-axis to urge the central anvil member to rotate about the second point toward the tilted position.

In one implementation, the central anvil member includes a generally planar portion and a hinge connector portion. The hinge connector portion extends outwardly from a central portion of a first surface of the generally planar portion. The first surface of the generally planar portion defines a plurality of staple engaging recesses adjacent a portion of a perimeter thereof. In the transverse position, the first surface of the generally planar portion is substantially parallel to the transverse plane. In addition, the anvil plates include a first anvil plate and a second anvil plate. The anvil plates are generally planar, are disposed laterally adjacent the central anvil member, and are hingedly connected to the central anvil member. Each anvil plate defines a plurality of staple engaging recesses adjacent a portion of a perimeter thereof on a first surface of each anvil plate. When the anvil plates are in the open position, the first surfaces of the anvil plates and the first surface of the generally planar portion of the central anvil member are substantially parallel to the transverse plane and face toward the surgical staple dispensing head.

Furthermore, the cable may have a first end, a second end, and a central portion there between. The first end of the cable is connected to the first anvil plate, and the second end of the cable is connected to the second anvil plate. The central portion of the cable extends through the central anvil member to an actuating mechanism. The actuating mechanism may be in the handle and is configured for selectively applying and releasing tension on the cable. Releasing tension on the cable urges the plates into the closed position, and applying tension to the cable urges the plates into the open position. In addition, the anvil assembly may include at least one spring loaded hinge assembly. The spring loaded hinge assembly hingedly attaches the central anvil member and each anvil plate. The spring loaded hinge assembly also includes a hinge spring between the central anvil member and each anvil plate to urge the plates toward the closed position.

In another implementation, the central anvil member includes a rod and a hinge connector portion that extends from a proximal end of the rod. A portion of a cable extends through the rod adjacent a distal end of the rod to each anvil plate. For example, the cable may have a first end, a second end, and a central portion there between. The first end of the cable may be connected to a first anvil plate, and the second end of the cable may be connected to a second anvil plate. The central portion of the cable may extend through the central anvil member to an actuating mechanism in the handle. The actuating mechanism is configured for selectively applying and releasing tension on the cable. In particular, in this implementation, releasing tension on the cable urges the plates into the open position and applying tension to the cable urges the plates into the closed position.

In addition, each plate defines a plurality of staple engaging recesses adjacent at least a portion of a perimeter thereof on a first surface of each plate. The anvil plates are substantially semi-annularly shaped and, in the open position, the first surfaces thereof are disposed in the same plane and together form a generally annular shape. The generally annular shape defines a central hole there through. The rod of the central anvil member extends through the central hole. Furthermore, each of the first and second anvil plates includes a first end and a second end. The anvil assembly further includes a first hinge connecting the first and second anvil plates at the first ends thereof and a second hinge connecting the first and second anvil plates at the second ends thereof.

According to various implementations, a method of using a surgical stapling apparatus includes: (1) providing a surgical stapling apparatus, such as, for example, the apparatus described above; (2) inserting the anvil assembly and surgical stapling head into a hole in a body with the anvil plates in the closed position and the central anvil member of the anvil assembly in the tilted position; (3) urging the central anvil member into the transverse position; (4) urging the anvil plates into the open position; (5) urging the anvil plates and central anvil member toward the surgical stapling head; (6) firing a plurality of staples from the surgical stapling dispensing head; (7) urging the anvil plates toward the closed position and the central anvil member toward the tilted position; and (8) withdrawing the anvil assembly and the surgical stapling dispensing head from the hole in the body.

In one implementation, the central anvil member is hingedly connected to the anvil plates, and urging the anvil plates into the open position includes tensioning one or more cables that extend between the central anvil member and each anvil plate. In addition, first surfaces of the anvil plates and the central anvil member define a plurality of staple engaging recesses adjacent at least a portion of a perimeter of each anvil plate and the central anvil member. The first surfaces of the anvil plates and the central anvil member are substantially parallel to the transverse plane in the opened and transverse positions. When the anvil plates and the central anvil member are in the opened and transverse positions, one or more staple engaging recesses defined adjacent an edge of each anvil plate align with one or more staple engaging recesses defined adjacent an edge of the central anvil member.

In another implementation, one or more cables connect the central anvil member to the anvil plates. Urging the anvil plates into the open position includes releasing tension on the one or more cables to allow the anvil plates to fold outwardly into the transverse plane.

BRIEF DESCRIPTION OF THE DRAWINGS

FIG. 28A illustrates inserting the anvil assembly in the closed and tilted positions through a hole in the new stomach pouch. FIG. 28B illustrates the anvil assembly fully within the new stomach pouch. FIG. 28C illustrates the anvil assembly in the transverse and open positions within the new stomach pouch. And, FIG. 28D illustrates the anvil assembly engaged against the surgical stapling head to perform the anastomosis between the new stomach pouch and the small intestine.

DETAILED DESCRIPTION

Various implementations of the invention provide for a one-piece surgical stapling apparatus that includes a stapler head and an anvil head assembly. The anvil head assembly is tiltable between a tilted position and a transverse position, and anvil plates of the anvil head assembly are moveable about one or more hinges between a closed and an open position. When in the tilted and closed positions, the anvil assembly has a reduced footprint that allows the anvil assembly to be passed directly through a trocar and holes created in the bodily tissues, which eliminates the need for separate placement of the anvil head. At the site of the anastomosis, the anvil head assembly can be moved to the transverse and open positions, and the stapling head may be engaged to fire staples against the anvil head.

Figure 1:
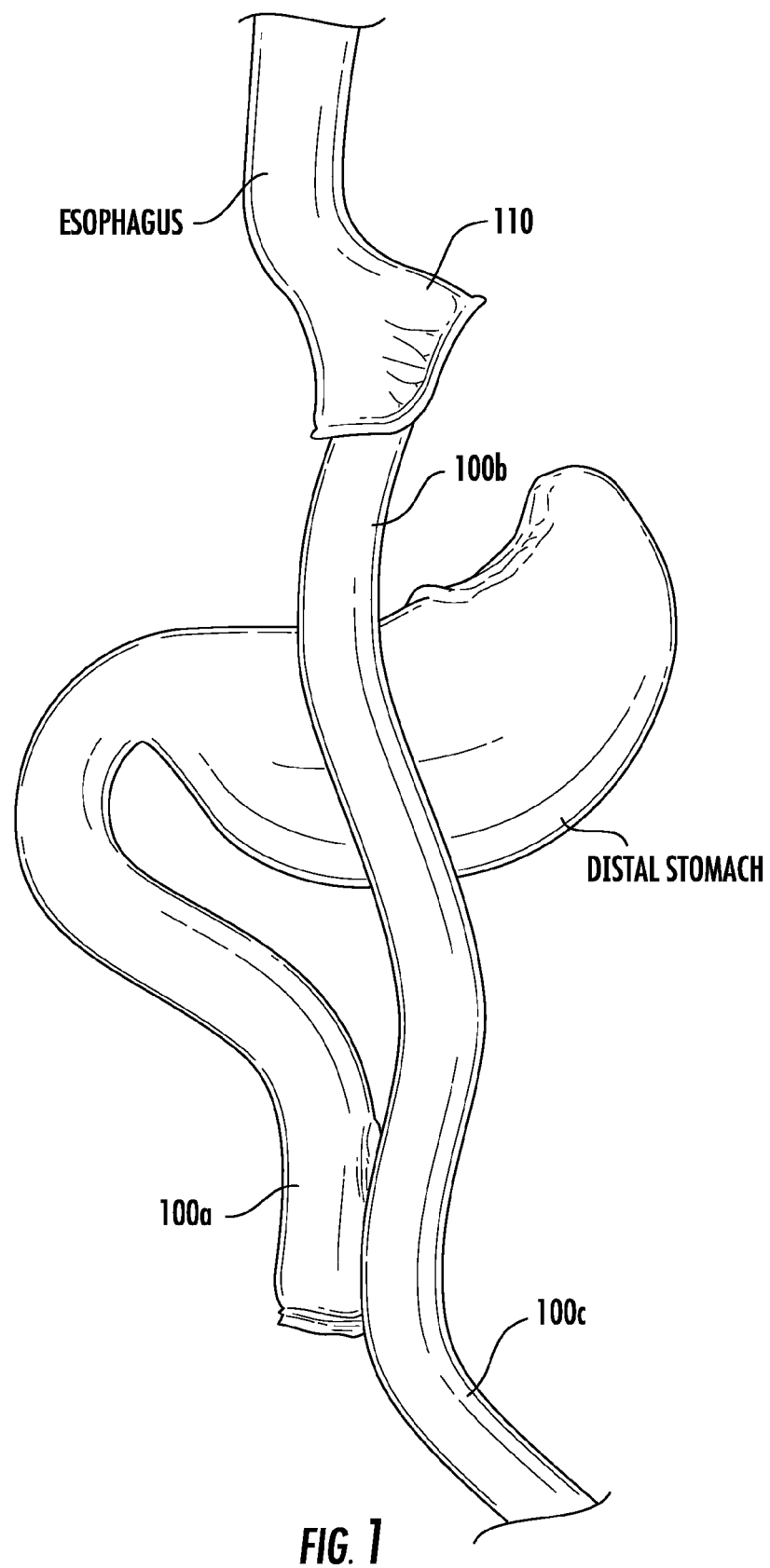
FIG. 1 illustrates a schematic view of roux-en-y gastric bypass.
Figure 2B:
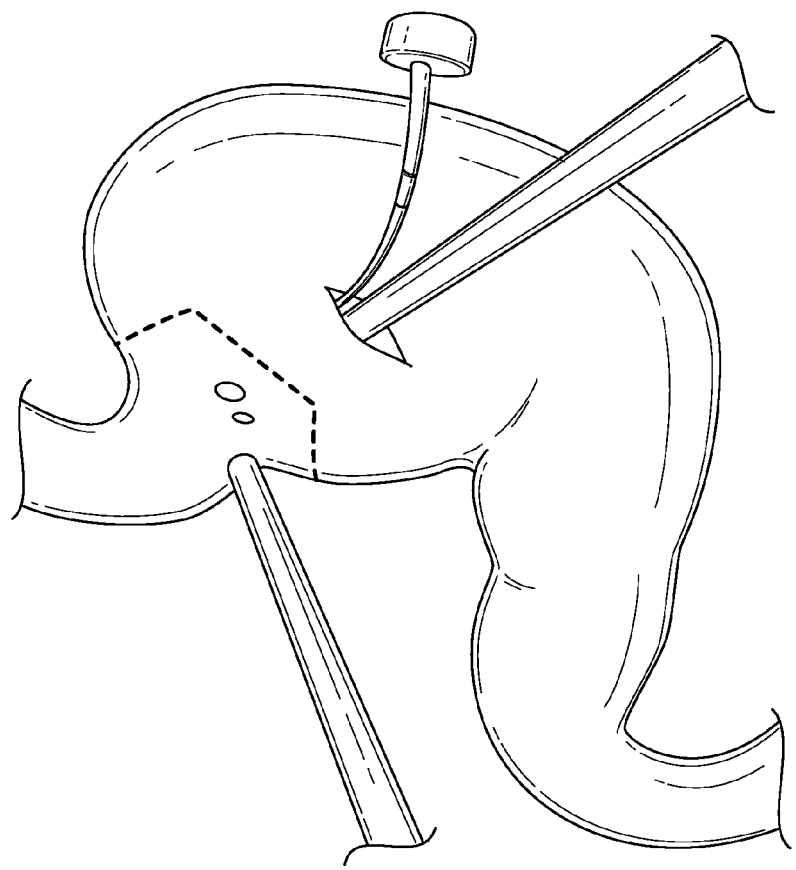
FIGS. 2A and 2B illustrate an exemplary roux-en-y gastric bypass procedure using a two-piece stapling apparatus.
Figure 2A:
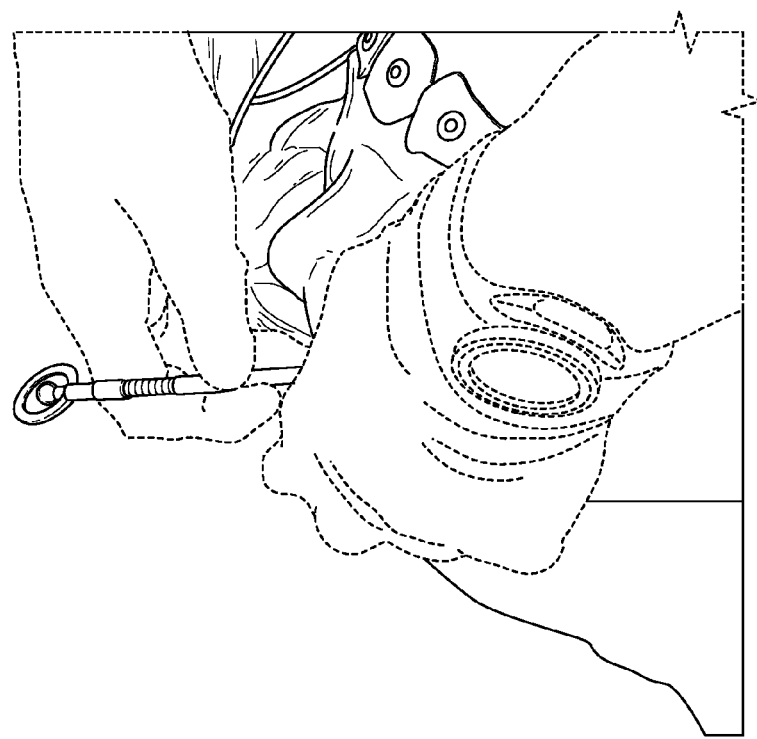
Figure 3:
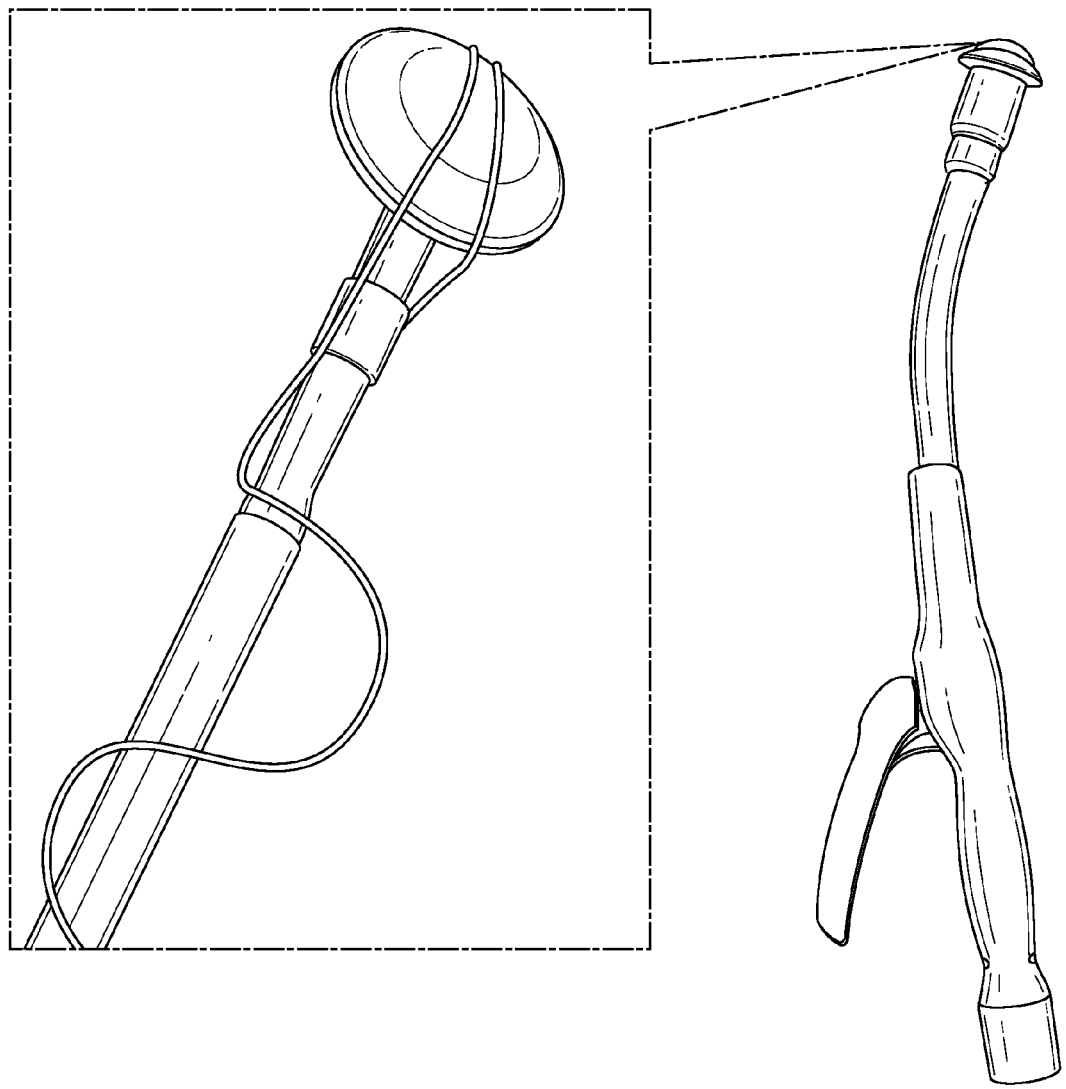
FIG. 3 illustrates a two-piece prior art surgical stapling apparatus after assembly of the anvil head to the stapling head within the body.
Figure 4:
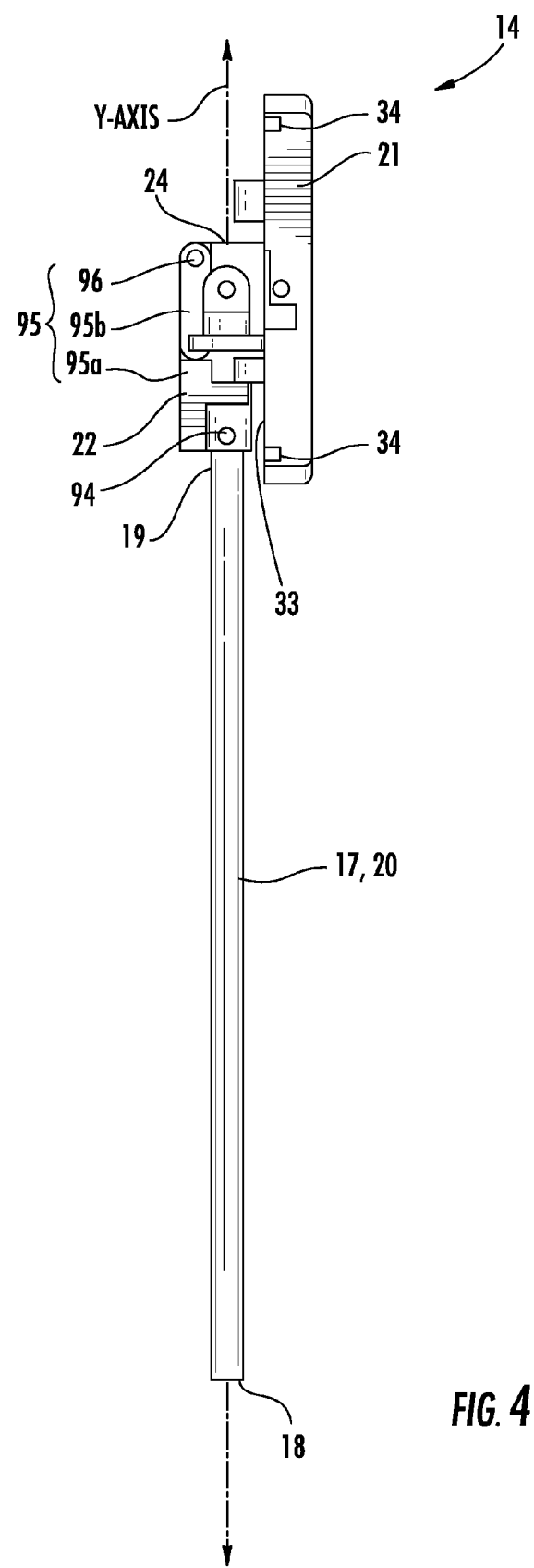
FIG. 4 illustrates a side view of a portion of an anvil assembly in a tilted position according to one implementation.
Figure 5:
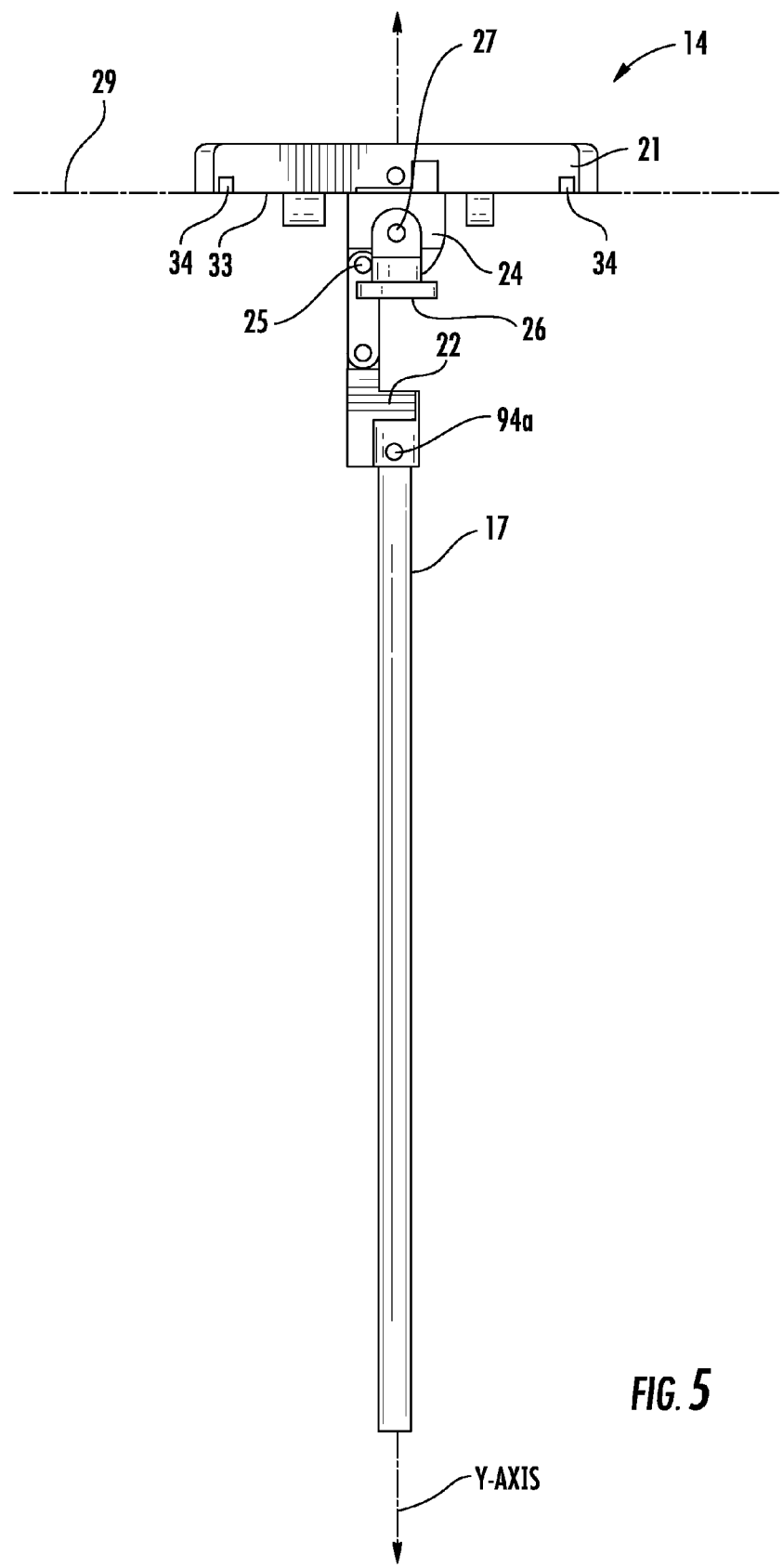
FIG. 5 illustrates a side view of a portion of the anvil assembly of FIG. 4 in a transverse position.
Figure 6:
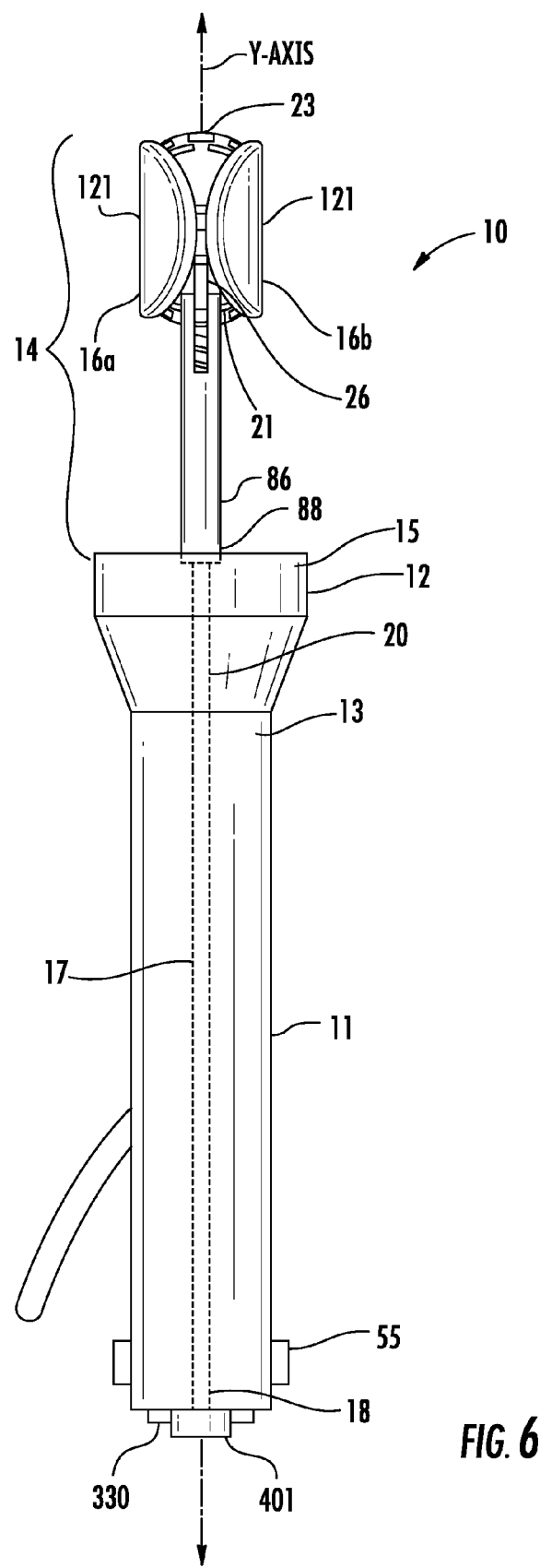
FIG. 6 illustrates a front view of the anvil assembly of FIG. 4 in the tilted and closed positions.

FIGS. 4-13 illustrate a surgical stapling apparatus 10 according to one implementation. As shown in FIG. 6, the apparatus 10 includes a handle 11, a surgical staple dispensing head 12 disposed adjacent a distal end 13 of the handle 11, and an anvil assembly 14 disposed adjacent a distal end 15 of the surgical staple dispensing head 12. As shown in FIGS. 4-13, the anvil assembly 14 includes a plunger 17 that has a proximal end 18, a distal end 19, and a central portion 20 there between, two anvil plates 16a, 16b that are separately formed from each other, a central anvil member 21, and a anvil rod 86 having a fixed hinge 26 at a distal end 87 thereof.

Figure 9:
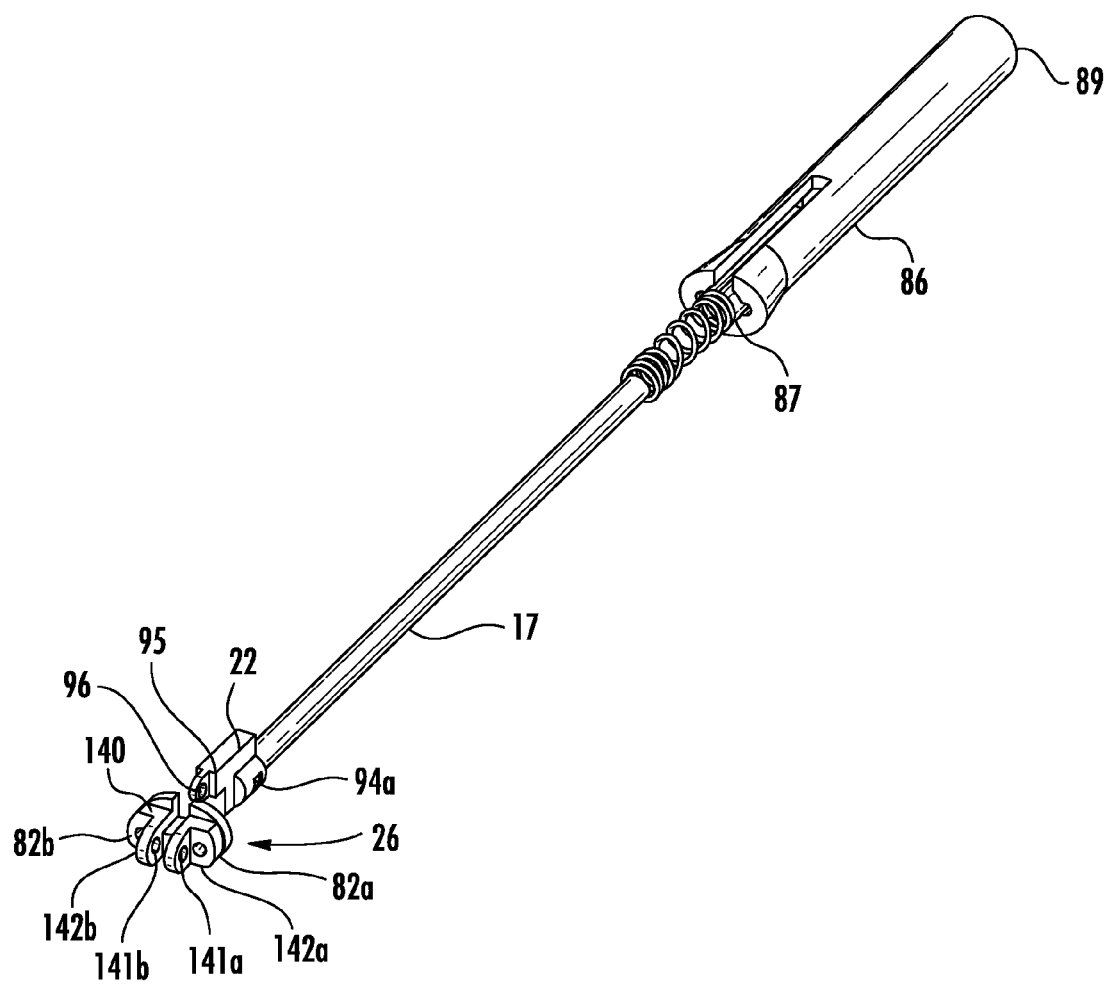
FIG. 9 illustrates a perspective view of portions of the anvil assembly shown in FIG. 6.

As shown in FIGS. 4, 5, and 9, the plunger 17 includes a plunger head 22 at the distal end 19 of the plunger 17. The plunger head 22 defines ports 94 through each side of the plunger head 22, and the ports 94 lead to an internal channel (not shown) that extends through the plunger 17 to the proximal end 18. The plunger head 22 also includes an extension portion 95 that extends upwardly along an axis that is offset from and substantially parallel to a y-axis. The y-axis extends from a proximal end of the handle 11 to a distal end 23 of the anvil assembly 14 through the central portion 20 of the plunger 17. The extension portion 95 defines a hole 96 through which a hinge pin may be inserted to connect the extension portion 95 of the plunger head 22 to the central anvil member 21, as described in below. As shown in FIG. 4, the extension portion 95 includes a first portion 95a that is integrally formed with the plunger head 22 and a second portion 95b that is connected to the first portion and extends upwardly from it. In other implementations, such as with the implementation shown in FIGS. 14-21, the extension portion 95 is one piece and is integrally formed with the plunger head 22.

Figure 10:
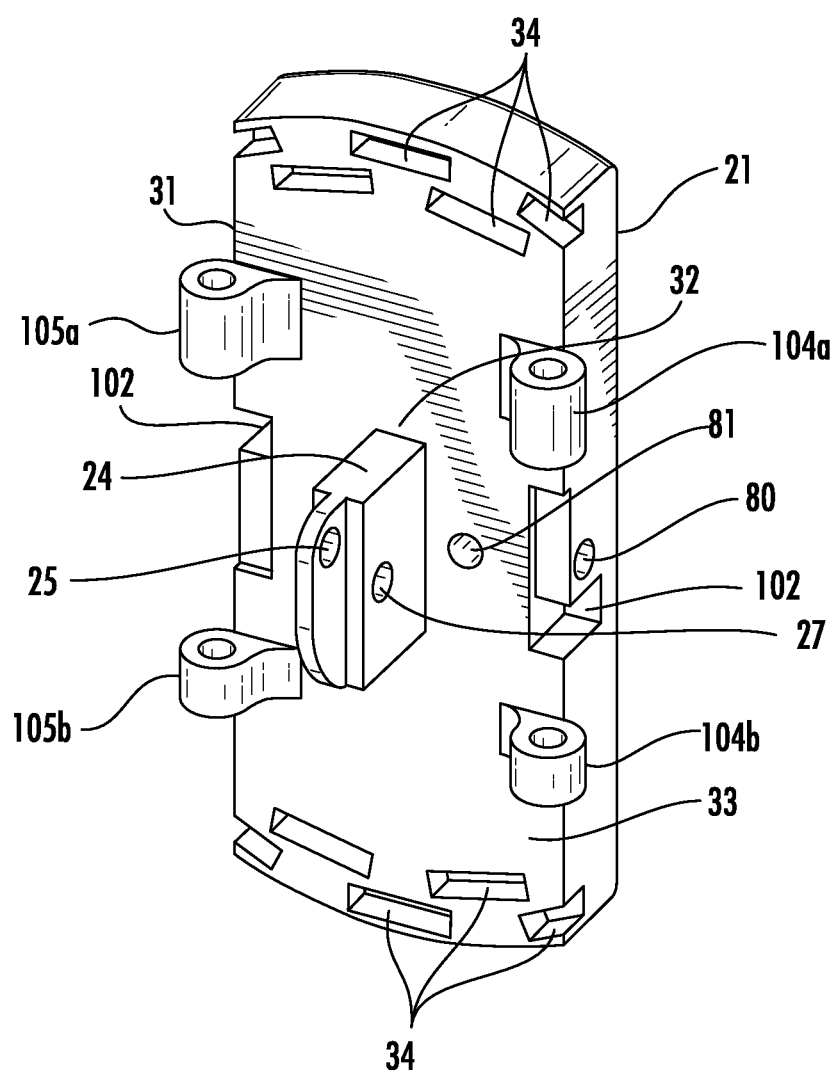
FIG. 10 illustrates a perspective view of a central anvil member as shown in FIG. 4.

As shown in FIG. 10, the central anvil member 21 includes a generally planar portion 31 and a hinge connector portion 24. The hinge connector portion 24 extends outwardly from a central portion 32 of a first surface 33 of the generally planar portion 31. The first surface 33 of the generally planar portion 31 defines a plurality of staple engaging recesses 34 adjacent a portion of a perimeter thereof. In addition, the hinge connector portion 24 defines a first hole 25 and a second hole 27 that extend through the hinge connector portion 24.

As shown in FIGS. 6, 7, 8, and 12, anvil plates 16a, 16b are generally planar and semi-circular shaped and have a first surface 124 that defines a plurality of staple engaging recesses 125 along a portion of a perimeter thereof, an exterior side 120, and an interior oriented side 121. Annular hinge portions 106a, 106b extend from the first surface 124 adjacent the interior oriented side 121. In addition, a spring leg channel 103 is defined between the hinge portions 106a, 106b. Furthermore, a cable connection portion 127 is defined in the first surface 124 between the hinge portions 106a, 106b.

Figure 13:
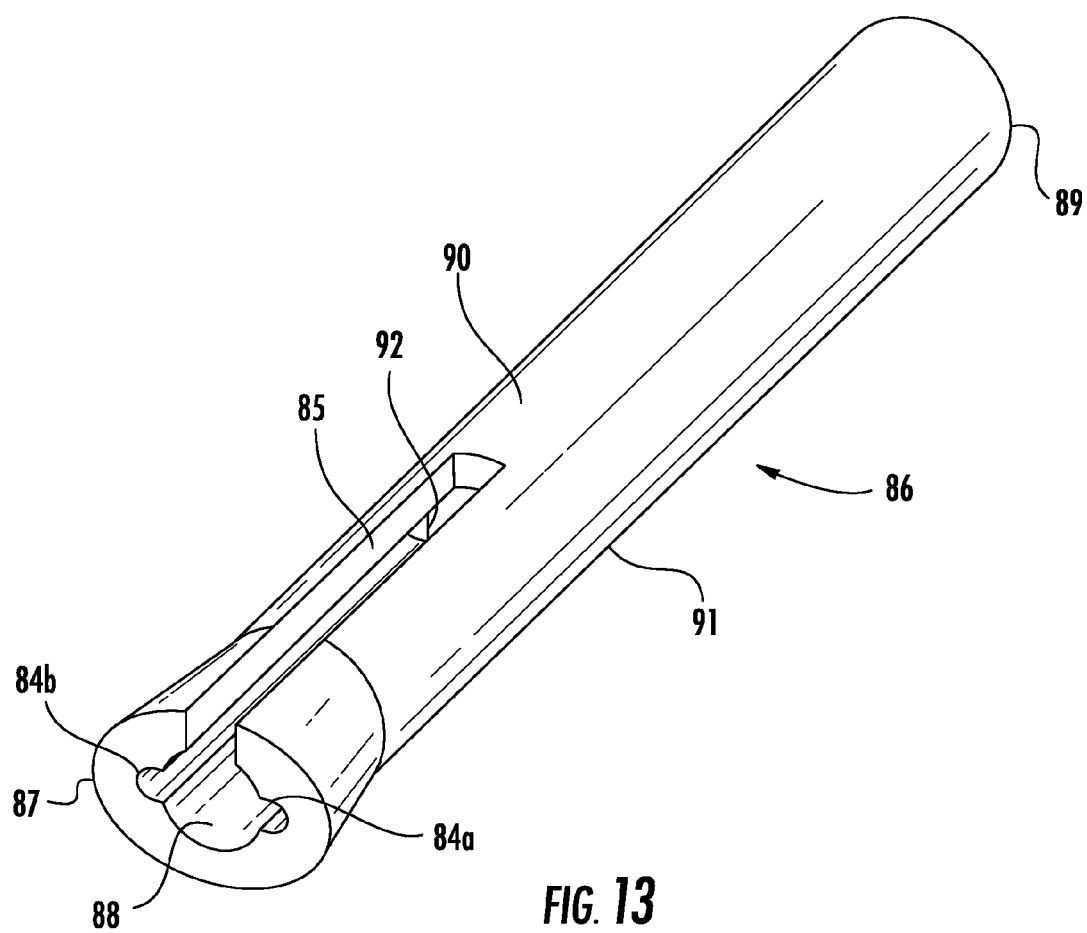
FIG. 13 illustrates a perspective view of a rod as shown in FIG. 6.

As shown in FIGS. 6, 9, and 13, the fixed hinge 26 is disposed adjacent the distal end 87 of the anvil rod 86. The fixed hinge 26 includes a base 140 that is attached to the anvil rod 86 and extension portions 141a, 141b that extend substantially perpendicularly from the base 140 in a direction substantially parallel to the y-axis. Channels 82a, 82b are defined through the base 140 and are disposed on opposite sides of the extension portions 141a, 141b, respectively. The extension portions 141a, 141b are spaced apart about the y-axis and each define a hole 142a, 142b, respectively, therethrough.

As shown in FIGS. 6, 7, 9, and 13, the anvil rod 86 defines an internal channel 88 extending between the proximal end 89 and the distal end 87 through which a portion of the plunger 17 extends. The anvil rod 86 also defines a longitudinal channel 85 extending between the internal channel 88 and an exterior surface 90 of the anvil rod 86. The longitudinal channel 85 extends from the distal end 87 of the anvil rod 86 toward a central portion 91 of the anvil rod 86 that is between the proximal end 89 and the distal end 87. The internal channel 88 further defines an internal annular ledge 92 and side channels 84a, 84b. A coiled compression spring is disposed between the internal annular ledge 92 and the distal end 18 of the plunger 17 adjacent the plunger head 22 and biases the plunger head 22 toward from the fixed hinge 26. In the implementation shown, the plunger 17 extends through a channel defined by the coiled compression spring. However, in alternative implementations, other types of springs may be used and the plunger 17 may not extend through a portion of the spring.

Figure 11:
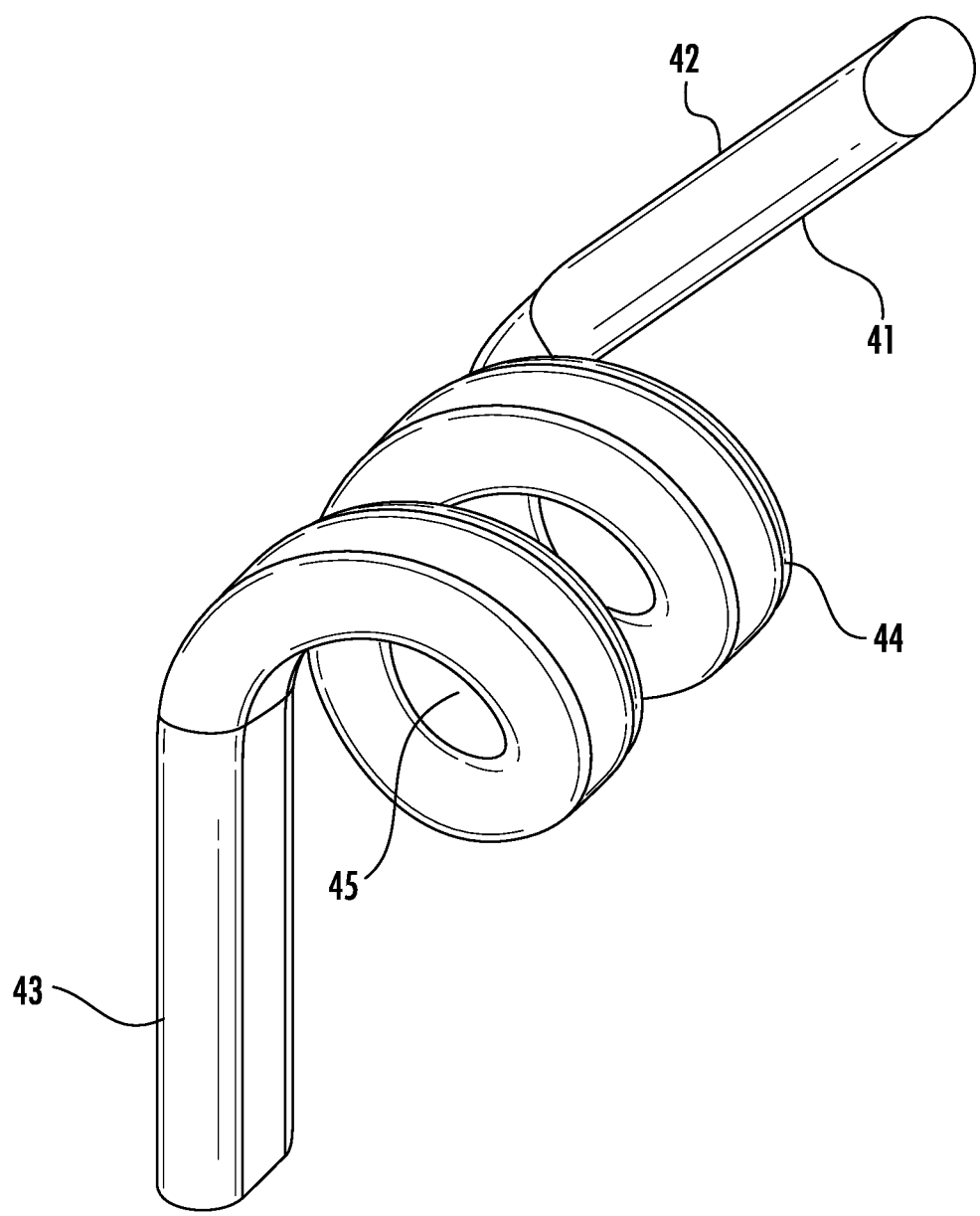
FIG. 11 illustrates a perspective view of a hinge spring as shown in FIG. 7.
Figure 12:
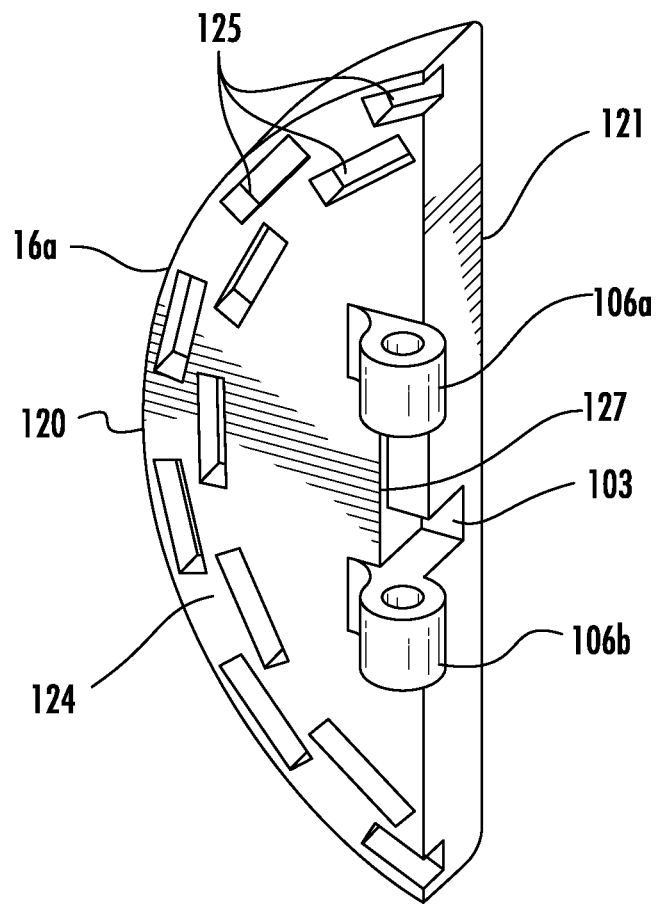
FIG. 12 illustrates a perspective view of an anvil plate as shown in FIG. 6.

In addition, the anvil assembly 14 includes at least one spring loaded hinge, as shown in FIG. 11, disposed between the central anvil member 21 and each anvil plate 16a, 16b. In the implementation shown, the spring loaded hinges are biased to urge the plates 16a, 16b into the closed position. The spring loaded hinge includes a hinge spring 41, which is shown in FIG. 11, that has an upper leg 42, a lower leg 43, and a spiral portion 44 that defines a channel 45 there through. The spring loaded hinge also includes the annular hinge portions 104a, 104b, 105a, 105b that extend from the first surface 33 of the central anvil member 21, the annular hinge portions 106a, 106b that extend from the first surfaces 124 of the anvil plates 16a, 16b, and hinge pins (not shown) that extend through the annular hinge portions 104a-b, 105a-b, and 106a-b and the channel 45 of the hinge spring 41. Furthermore, as shown in FIGS. 10 and 12, indention 102 receives one of the upper leg 42 or lower leg 43 of the first hinge spring 41, and indentation 103 on the interior oriented side surface of anvil plate 16a, 16b receives the other of the upper leg 42 or the lower leg 43 of the hinge spring 41 when the anvil plates 16a, 16b are hingedly connected to the central anvil member 21 via hinge pins.

Figure 7:
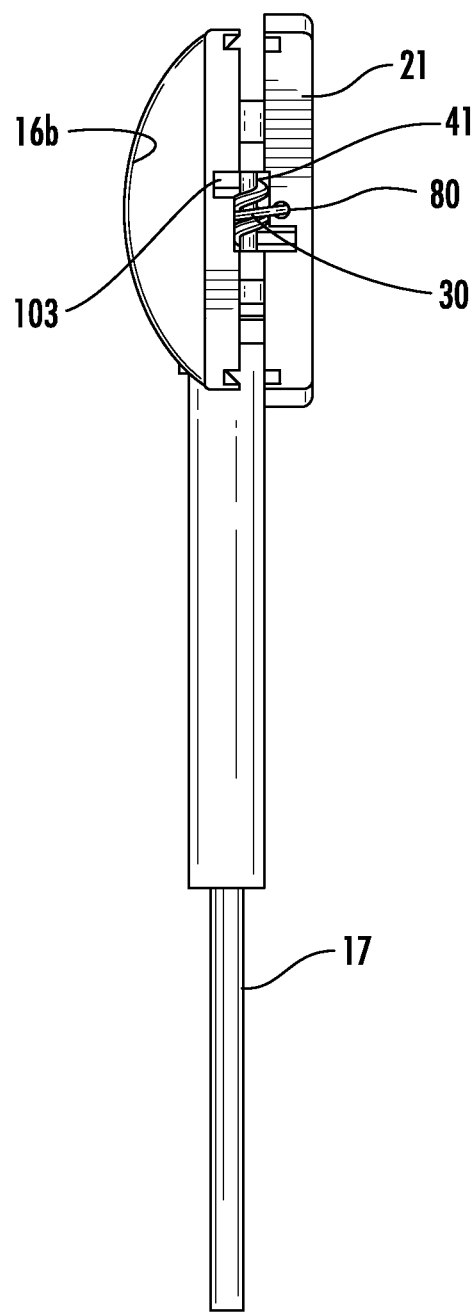
FIG. 7 illustrates a side view of the anvil assembly in FIG. 6.

As shown in FIG. 7, the anvil assembly 14 includes a cable 30 that extends between the anvil plates 16a, 16b and the central anvil member 21. The cable 30 is configured for urging the anvil plates 16a, 16b between a closed position and an open position. In the open position, which is shown in FIG. 5, the anvil plates 16a, 16b are disposed substantially parallel to the transverse plane 29. In the closed position, which is shown in FIG. 6, the anvil plates 16a, 16b are not parallel to the transverse plane 29. The cable 30 may be stainless steel, such as 316 stainless steel, or other suitable medical grade material.

As shown in FIGS. 7, 10 and 13, a first end of the cable 30 is attached to the first anvil plate 16a and a second end of the cable 30 is attached to the second anvil plate 16b. The central portion of the cable 30 between the first and second ends thereof extends through the anvil assembly toward one or more actuating mechanisms in the handle 12, such as the actuating mechanisms 40, 50, 83 described below in relation to FIGS. 29, 30, and 31, respectively. In particular, a central portion of the cable 30 is attached to one or more actuating mechanisms in the handle 12. The first and second ends of the cable 30 are thread upwardly through the internal channel of the plunger 17, out of ports 94 in the plunger head 22, through channels 82a, 82b defined in base 140 of the fixed hinge 26, into first surface ports 81 defined on the first surface 33 of the central anvil member 21, through channels defined through the central anvil member 21, and out of side ports 80 defined on each side of the central anvil member 21. The first and second ends are then secured in each anvil plate 16a, 16b, respectively, in the cable connection portions 127.

The first hole 25 in the hinge connector portion 24 of the central anvil member 24 is aligned with the hole 96 in the extension portion 95 of the plunger head 22 and a hinge pin is engaged within the holes 25, 96 to hingedly connect the hinge connector portion 24 to the plunger head 22. In addition, the second hole 27 in the hinge connector portion 24 is aligned with the holes 142a and 142b of the fixed hinge 26, and a hinge pin is engaged within the holes 27, 142a, 142b to hingedly connect the hinge connector portion 24 with the fixed hinge 26. The proximal end 18 of the plunger 17 is coupled to a linear actuating mechanism in the handle 12, such as mechanism 40, 50, or 83 described below in relation to FIG. 29, 30, or 31, respectively. The primary actuating mechanism in the handle 12 is configured for translating the plunger 17 downwardly along the y-axis to urge the central anvil member 21 to rotate about the second hole 27 toward a transverse position and for translating the plunger 17 upwardly along the y-axis to urge the central anvil member 21 to rotate about the second hole 27 toward a tilted position. In the transverse position, the first surface 33 of the central anvil member 21 is substantially parallel to a transverse plane 29 that extends substantially perpendicularly to the y-axis. In the tilted position, the first surface 33 of the central anvil member 22 is not parallel to the transverse plane 29.

As shown in FIG. 6, a proximal end 89 of the anvil rod 86 is disposed adjacent the surgical staple dispensing head 12, and the longitudinal channel 85 extending from the distal end 87 of the anvil rod 86 is provided to allow a portion of the plunger head 22 to extend through the longitudinal channel 85 during translation of the plunger 17 along the y-axis.

Figure 8:
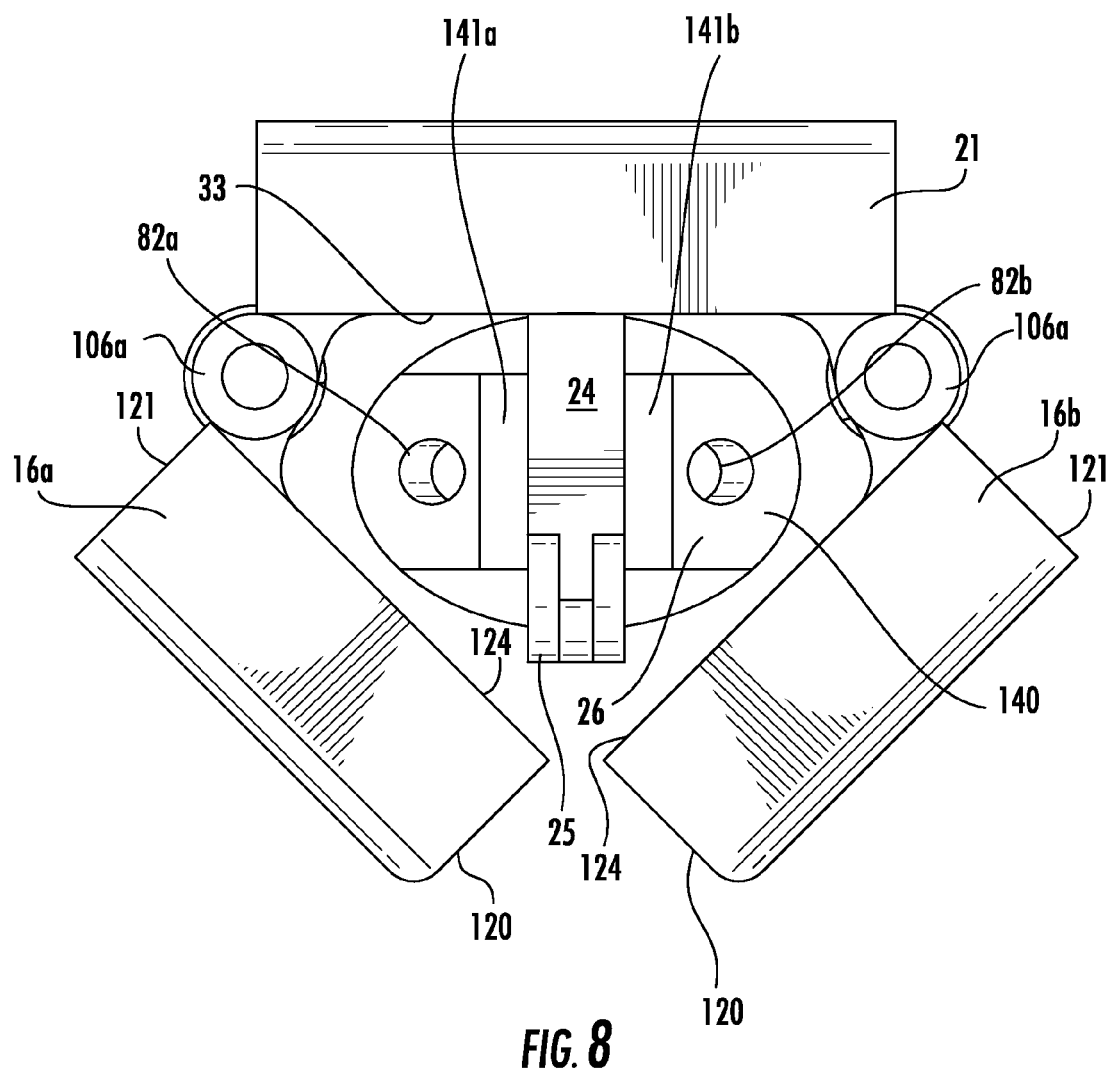
FIG. 8 illustrates a top view of the anvil assembly in FIG. 6.
Figure 30:
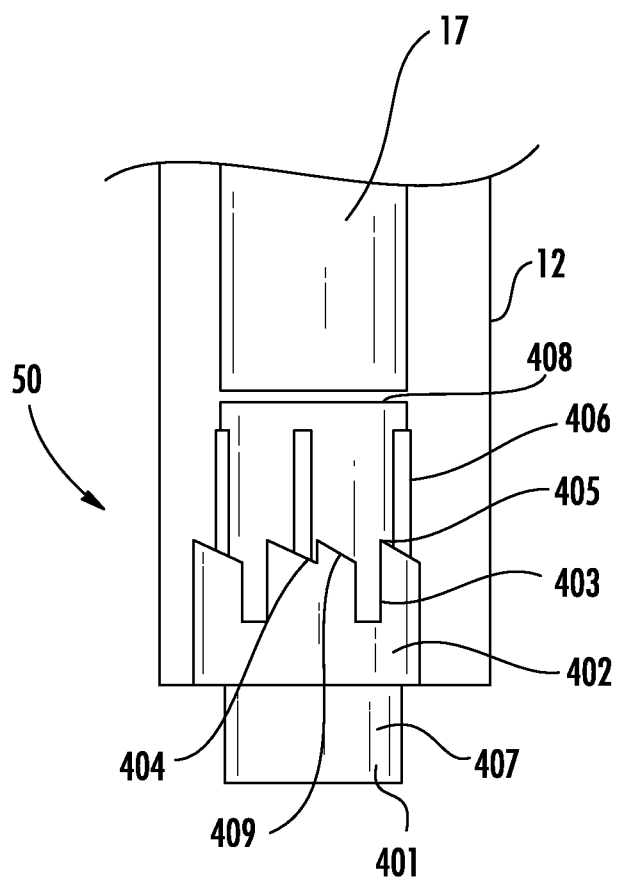
FIG. 30 illustrates a secondary actuating mechanism according to one implementation.

After the central anvil member 21 and anvil plates 16a, 16b have been moved from the tilted position to the transverse position, the anvil plates 16a, 16b may be moved from a closed position, such as shown in FIG. 6-8, to an open position in which the first surfaces 124 of the anvil plates 16a, 16b are in substantially the same plane as the first surface 33 of the central anvil member 21. To actuate the anvil plates 16a, 16b to the open position, the cable 30 is tensioned sufficiently to overcome the biasing forces of the spring hinges 41. In the implementation shown in FIGS. 4-13, the central portion of the cable 30 is moved downwardly as the plunger 17 is translated downwardly to move the central anvil member 21 from the tilted position to the transverse position. In addition, a secondary actuating mechanism, such as mechanism 50 described below in relation to FIG. 30, is engaged to move the central portion of the cable 30 downwardly further to overcome the biasing force of the spring hinges 41. This secondary actuating mechanism allows the surgeon to move the anvil plates 16a, 16b and central anvil member 21 fully into the transverse position prior to moving the anvil plates 16a, 16b into the open position.

Once the anvil plates 16a, 16b and the central anvil member 21 are in the transverse and open positions, the plunger 17 and the anvil rod 86 are moved downwardly toward the surgical staple dispensing head 12 to an engagement position. In this engagement position, tissue is clamped between the anvil plates 16a, 16b and the central anvil member 21 and the surgical staple dispensing head 12. Once clamped, the stapling and cutting mechanism of the surgical staple dispensing head 12 can be engaged to create the anastomosis. The movement of the plunger 17 and the anvil rod 86 to the engagement position may be effected by one or more actuating mechanisms in the handle, such as those described in relation to FIG. 29, 30, or 31.

Figure 29:
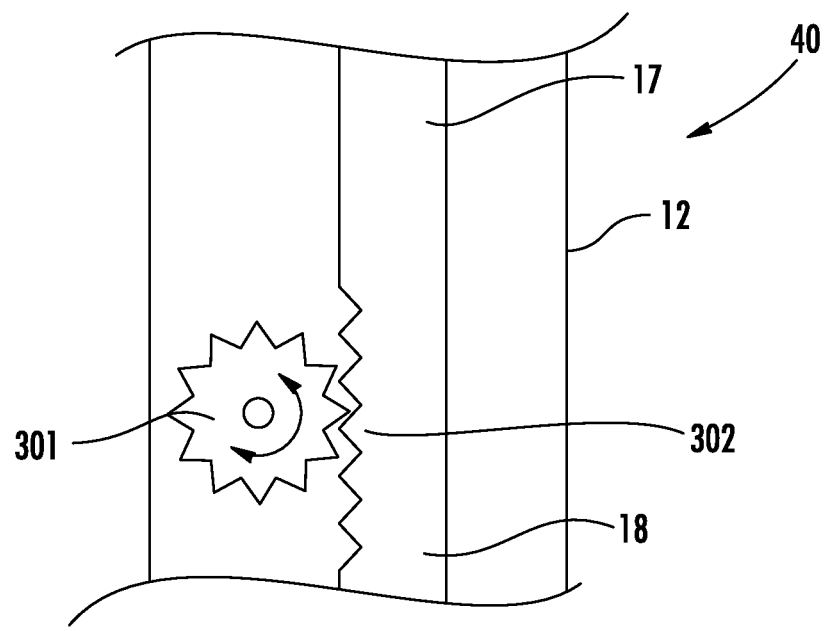
FIG. 29 illustrates a primary actuating mechanism according to one implementation.

FIG. 29 illustrates a linear actuating mechanism 40 according to one implementation. The linear actuating mechanism 40 includes a rack and pinion assembly. The pinion 301 is attached to a knob, such as knob 55, in the handle 11 that can be rotated. The rack 302 is defined on an exterior surface of the proximal end 18 of the plunger 17 and is engaged with the pinion 301. The knob 55 is rotated in a first direction to move the rack downwardly and in a second opposite direction to move the rack upwardly. In alternative embodiments, other known mechanisms for translating the plunger up or down along the y-axis may be used. Although this mechanism 40 is described as being used to translate the plunger 17 upwardly or downwardly between the transverse and tilted positions, it could also be used to move the move the distal end 89 of the anvil rod 86 upwardly or downwardly relative to the engagement position. Similarly, it may be used to selectively apply or release tension on the cable 30 to move the anvil plates 16a, 16b between the open and closed positions.

FIG. 30 illustrates an actuating mechanism 50 according to one implementation. The actuating mechanism 50 is disposed within the handle 11 and is configured for selectively applying or releasing tension on the cable 30. In the implementation described above in relation to FIGS. 4-13, releasing tension on the cable 30 urges the plates 16a, 16b into the closed position, and applying tension to the cable 30 urges the plates 16*a*, 16*b* into the open position. The actuating mechanism 50 is similar to the mechanism used in a retractable pen. In particular, the mechanism 50 includes an external cylinder 402 that defines one or more long grooves 403 and one or more short grooves 404 extending longitudinally from a distal end 405 of the external cylinder 402. In between the long grooves 403 and the short grooves 404 are slanted surfaces 409 that slant toward the grooves 403, 404 in the same direction. The actuating mechanism 50 also includes an internal cylinder 401 that is axially aligned with and movable within the external cylinder 402. The internal cylinder 401 defines one or more longitudinal protrusions 406 that extend radially outwardly from an external surface of the internal cylinder 401. A proximal end 407 of the internal cylinder 401 extends outwardly from the handle 11. A distal end 408 of the internal cylinder 401 abuts the proximal end 18 of the plunger 17. A proximal end 410 of each longitudinal protrusion 406 is slanted so as to mate with the slanted surface 409 on the external cylinder 402. The mating of the slanted surfaces 410, 409 causes the internal cylinder 401 to rotate such that the protrusions 406 alternately align with a long groove 403 or a short groove 404 in response to the proximal end 407 of the internal cylinder 401 being pushed axially inwardly. When the longitudinal protrusions 406 are engaged in the short grooves 404, the distal end 408 of the internal cylinder 401 moves the proximal end 18 of the plunger 17 upwardly, and when the longitudinal protrusions 406 are engaged in the long grooves 403, the distal end 408 of the internal cylinder 401 moves the proximal end 18 of the plunger 17 downwardly. The coiled compression spring disposed within the anvil rod 86 between the plunger head 22 and the internal annular surface 92 of the rod forces the longitudinal protrusions 406 into the grooves 403, 404. In operation, after the plunger 17 has been urged downwardly to translate the central anvil member 21 and the anvil plates 16*a*, 16*b* into the transverse position, the surgeon can push the proximal end 407 of the internal cylinder 401 axially inwardly to rotate the internal cylinder 401 such that the longitudinal grooves 406 engage with the long grooves 403. This engagement allows the plunger to move downwardly a sufficient distance to tension the cable 30 fully so that the biasing force of the spring hinges 41 is overcome. Although this mechanism 50 is described as being used to selectively release or apply tension to the cable 30 to urge the anvil plates 16*a*, 16*b* between the open and closed positions, it may also be used to move the plunger 17 upwardly or downwardly to urge the anvil plates 16*a*, 16*b* into the transverse position. Similarly, it may be used to move the distal end 89 of the anvil rod 86 downwardly or upwardly relative to the engagement position.

Figure 31:
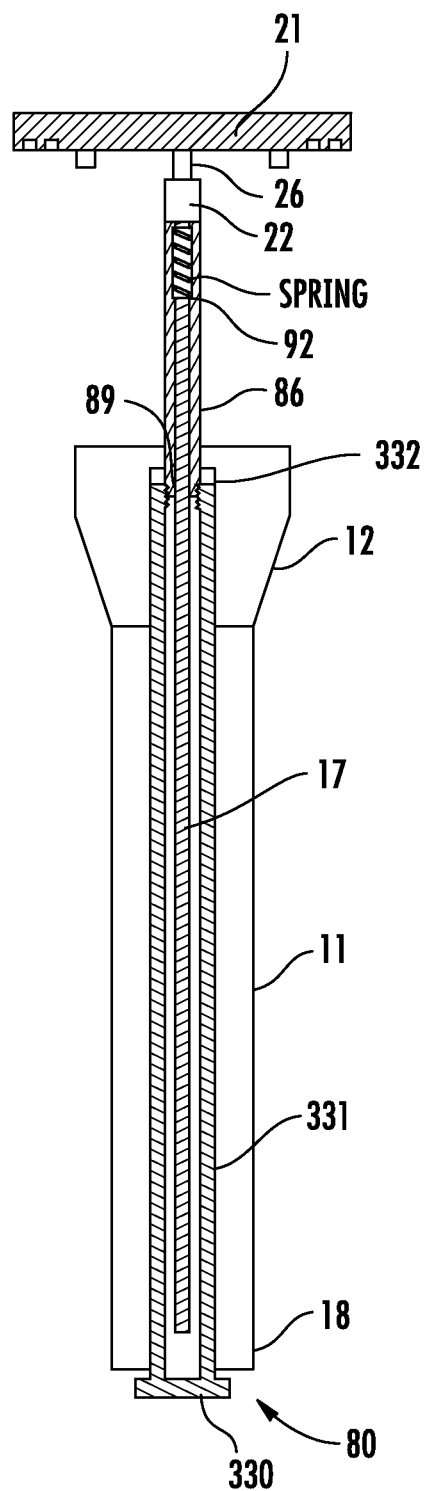
FIG. 31 illustrates a third actuating mechanism as used with the apparatus described in FIG. 9.

FIG. 31 illustrates another implementation of an actuating mechanism 83 according to one implementation. In particular, a rotatable knob 330 is disposed adjacent the proximal end 18 of the handle 11. The knob 330 includes a shaft 331 that is threaded adjacent its distal end 332. The shaft 331 is hollow and allows the plunger 17 to pass through it. The anvil rod 86 defines a threaded portion 332 adjacent its proximal end 89 that engages the threaded portion of the shaft 331. Upon rotation of the knob 330 in a first direction, the fixed hinge 26 of the anvil rod 86 is urged toward the surgical staple dispensing head 12, and upon rotation of the knob 330 in a second, opposite direction, the fixed hinge 26 of the anvil rod 86 is urged away from the surgical staple dispensing head 12. As shown, the threaded portion 332 of the shaft 331 is defined on an internal surface of the shaft 331 and the threaded portion of the anvil rod 86 is disposed on an external surface of the anvil rod 86. However, in other implementations, the threaded portion of the anvil rod 86 is defined on an internal surface of the anvil rod 86 and the threaded portion of the shaft 331 is defined on an external surface of the shaft 331. Although this mechanism 83 is described as being used to move the distal end 89 of the anvil rod 86 toward or away from the engagement position, this mechanism 83 could also be used to move the plunger 17 upwardly or downwardly to urge the central anvil member 21 between the tilted and transverse positions, or it could be used to selectively apply and release tension on the cable 30 to move the anvil plates 16*a*, 16*b* between the open and closed positions.

In addition, the mechanism 83 described in relation to FIG. 31 may be used with the mechanisms described in FIG. 29 or 30 to move the assembly into various positions. For example, the mechanism 40 described in relation to FIG. 29 may be used to translate the central anvil member 21 and anvil plates 16*a*, 16*b* between the transverse and tilted positions, the mechanism 50 described in relation to FIG. 30 may be used to move the anvil plates 16*a*, 16*b* between the open and closed positions, and the mechanism 83 described in relation to FIG. 31 may be used to move the distal end 89 of the anvil rod 86 downwardly or upwardly related to the engagement position. Alternatively, only one of these mechanisms may be used to perform two or more of these functions.

Another implementation of an anvil rod 186 and fixed hinge 126 is shown in FIGS. 14-21. The remaining portions of the anvil assembly 14 are similar to the implementation described above in relation to FIGS. 4-13 except as described below. The fixed hinge 126 defines two extension portions 241*a*, 241*b* that are spaced apart from each other and extend axially from the distal end 187 of the anvil rod 186. Between the extension portions 241*a*, 241*b*, a rod channel 188 is defined through which the plunger 17 extends. Each extension portion 241*a*, 241*b* includes an arcuate surface 242 extending from a distal end 193 of the fixed hinge 126 toward a front side 191 of the fixed hinge 126, and the arcuate surface 242 defines an arcuate channel 243 therein. The extension portions 241*a*, 241*b* also define holes 282*a*, 282*b*, respectively, that extend transversely there through.

The hinge connector portion 24 is disposed between the extension portions 241*a*, 241*b*, and the second hole 27 of the hinge connector portion 24 is aligned with the holes 282*a*, 282*b* of the fixed hinge 126. The first surface 33 of the central anvil member 21 is oriented to face the arcuate surfaces 242. A hinge pin is inserted through the holes 27, 282*a*, 282*b* to pivotably connect the hinge connector portion 24 with the fixed hinge 126. In addition, the portions of the cable 30 that extend between the ports 94 of the plunger head 22 and the central anvil member 21 are disposed within the arcuate channels 243. These arcuate channels 243 protect the cable 30 as the central anvil member 21 is rotated between the tilted and transverse positions. In addition, in this implementation, an actuating mechanism for applying or releasing tension on the cable, such as mechanism 50 described above in relation to FIG. 30, may not be used because the arc length of these channels 243 provides the additional length that the cable needs to be tensioned sufficiently after the plunger is translated downwardly to overcome the biasing force of the hinge springs 41.

Figure 14:
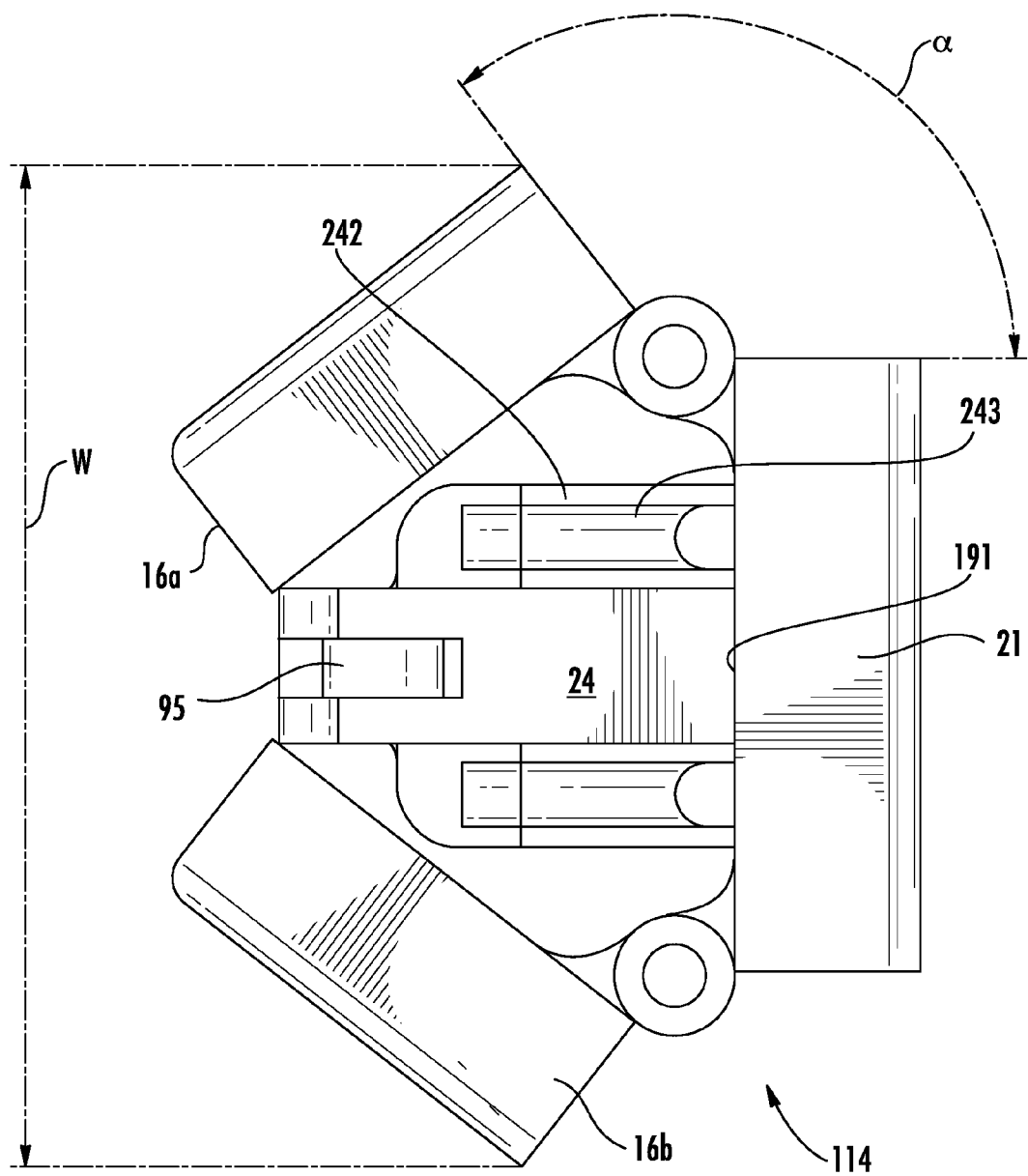
FIG. 14 illustrates a top view of an anvil assembly in the closed and tilted positions according to an alternative implementation.
Figure 15:
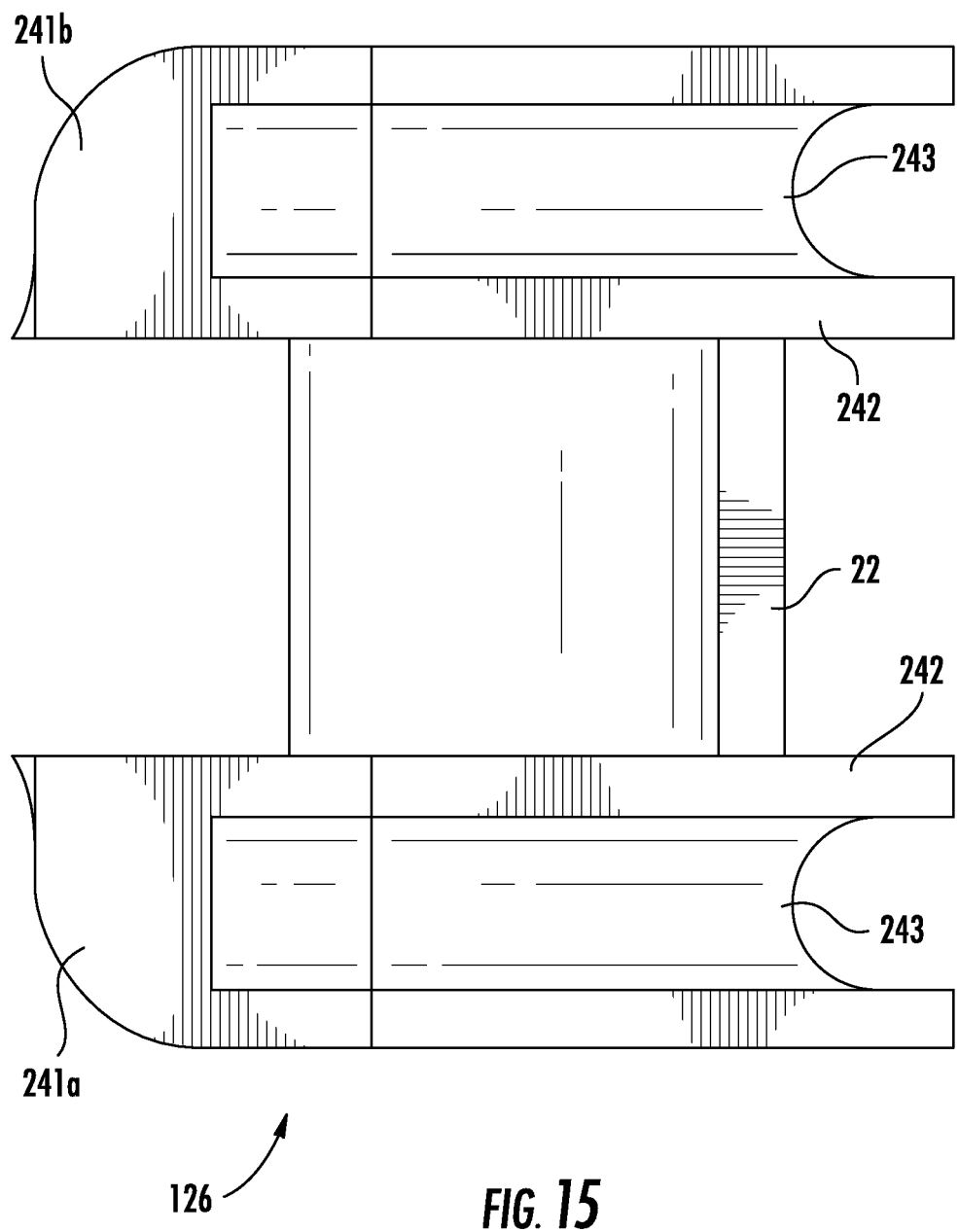
FIG. 15 illustrates a top view of the rod and fixed hinge of the anvil assembly shown in FIG. 14.
Figures 16, 17, 18, 19:
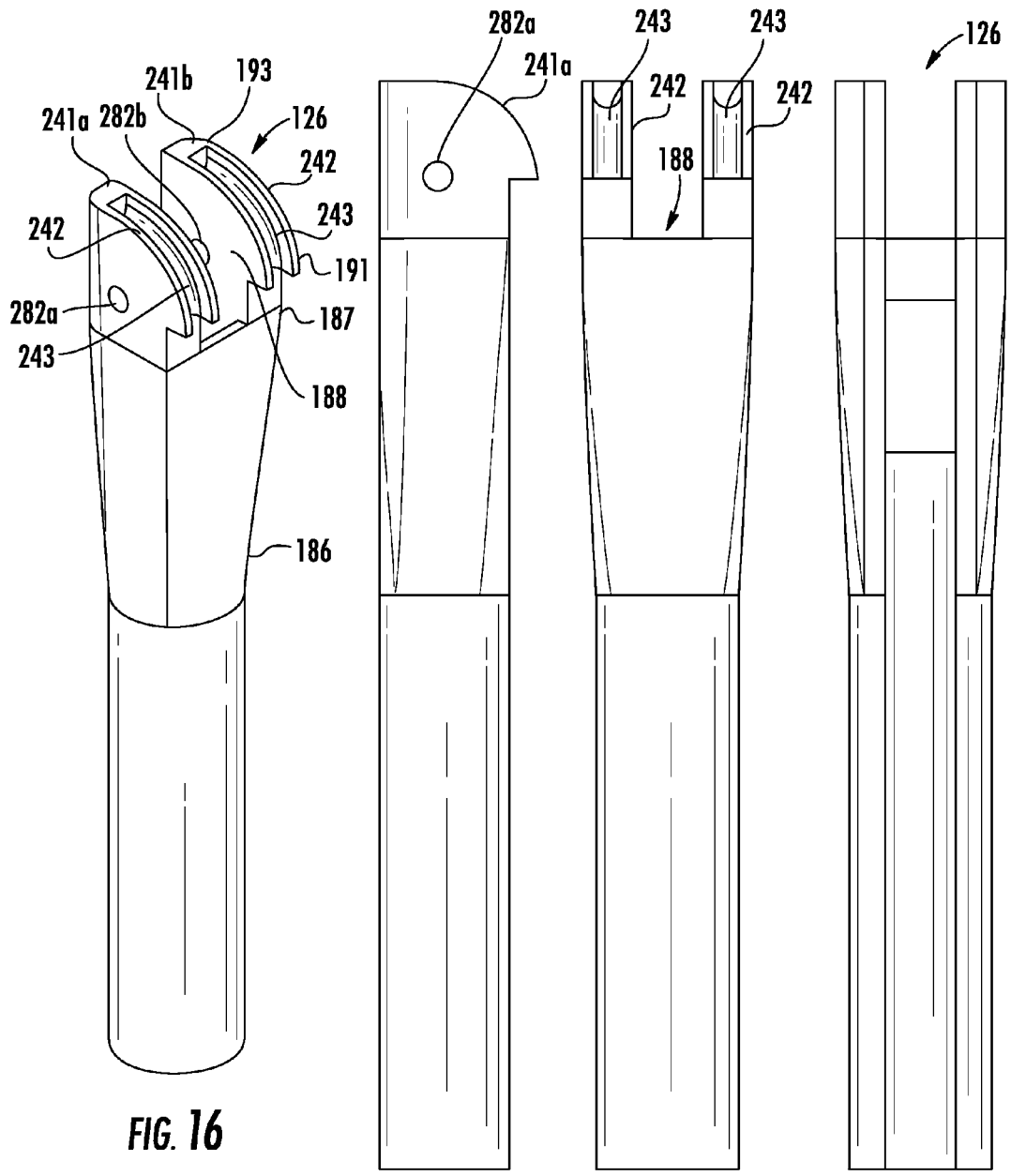
FIG. 16 illustrates a perspective view of the rod and fixed hinge shown in FIG. 15.
FIG. 17 illustrates a side view of the rod and fixed hinge shown in FIG. 15.
FIG. 18 illustrates a front view of the rod and fixed hinge shown in FIG. 15.
FIG. 19 illustrates a rear view of the rod and fixed hinge shown in FIG. 15.
Figure 20:
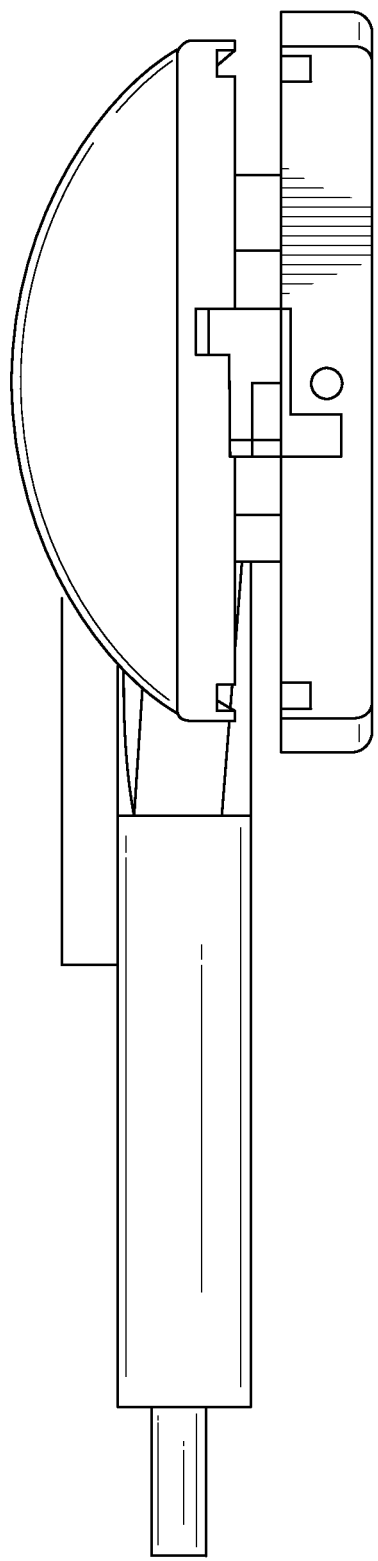
FIG. 20 illustrates a side view of the anvil assembly shown in FIG. 14.
Figure 21:
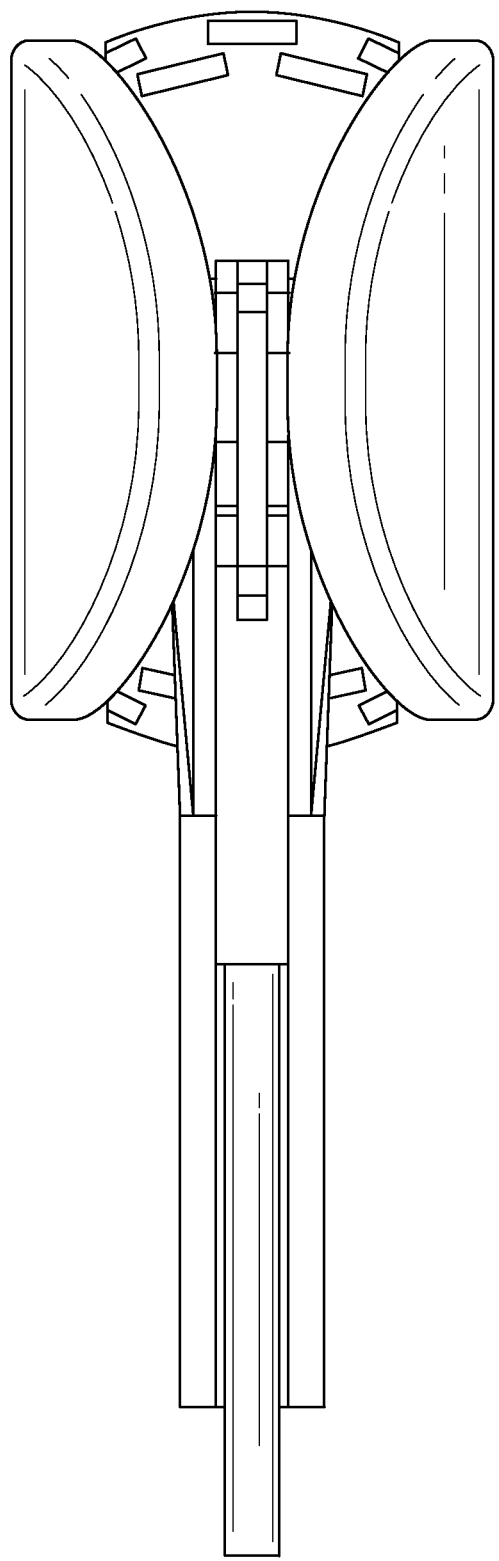
FIG. 21 illustrates a front view of the anvil assembly shown in FIG. 14.

In the closed and tilted positions, the anvil assembly 14 may be between about 10 mm and about 17 mm wide and deep, as denoted by w in FIG. 14. In addition, according to various implementations, the anvil plates 16a, 16b may rotate through an angle α of between about 120 degrees and about 130 degrees.

Another implementation of the anvil assembly 150 is shown in FIGS. 22-28D. In this implementation, the central anvil member 51 includes a rod 52 and a hinge connector portion 53 that extends from a proximal end 54 of the rod 52. The hinge connector portion 53 shown in FIGS. 23A-C is similar in operation to the hinge connector portion 24 described above in relation to FIGS. 4-13 but has two extension portions that flank a portion of the plunger head 22. A hinge pin (not shown) extends transversely through the hinge connector portion 53 and the plunger head 22. The anvil assembly 150 also includes two anvil plates 56a, 56b. Each anvil plate 56a, 56b is substantially semi-annularly shaped and includes a first end 63 and a second end 64. A first hinge 65 connects the anvil plates 56a, 56b at the first ends 63 thereof, and a second hinge 65 connects the anvil plates 56a, 56b at the second ends 64 thereof. The hinges 65 may be spring loaded and biased into the closed position or the open position.

A portion of the cable 30 extends through the rod 52 adjacent a distal end 55 of the rod 52 to each anvil plate 56a, 56b. For example, the first end 37 of the cable 30 is connected to the first anvil plate 56a, and the second end 38 of the cable 30 is connected to the second anvil plate 56b. The central portion 39 of the cable 30 may extend through the central anvil member 51 to one or more actuating mechanisms in the handle 11 or the proximal end 18 of the plunger 17. In this implementation, releasing tension on the cable 30 urges the plates 56a, 56b into the open position and applying tension to the cable 30 urges the plates 56a, 56b into the closed position.

In addition, each plate 56a, 56b defines a plurality of staple engaging recesses 60 adjacent at least a portion of a perimeter thereof on a first surface 61 of each plate 56a, 56b. In the open position, the first surfaces 61 of the anvil plates 56a, 56b are disposed in substantially the same plane and together form a generally annular shape. The generally annular shape defines a central hole 62 there through. The rod 52 of the central anvil member 51 extends through the central hole 62.

In the closed and tilted positions, the anvil assembly 150 may be between about 17 mm wide and about 6 mm deep as viewed from the side view shown in FIG. 23A. In addition, according to various implementations, the anvil plates 56a, 56b may rotate through an angle of between about 45° and about 90° between the closed and open positions and through an angle of between about 45° to about 90° between the tilted and the transverse positions. In the opened and transverse positions, the annular shaped ring defined by the anvil plates 56a, 56b may have an outer diameter of about 25 mm, and a height of the anvil assembly 150 from the distal end 55 of the central anvil member 51 to the anvil plates 56a, 56b is about 6 mm.

Figure 28A:
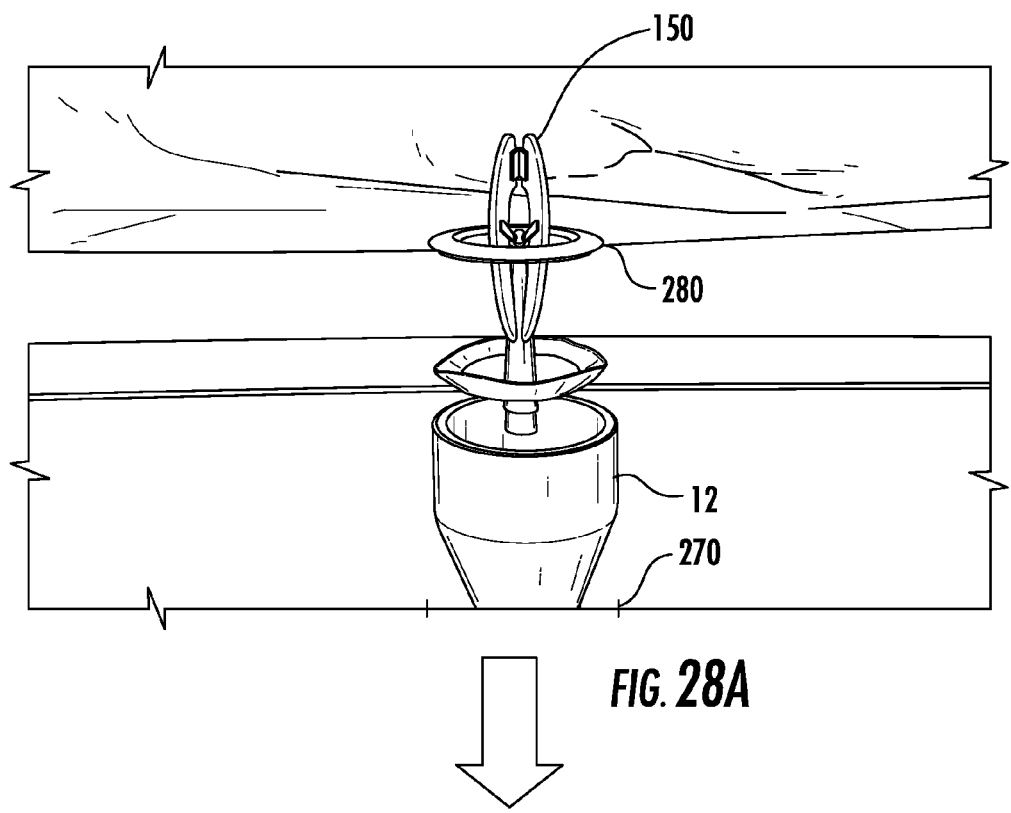
FIG. 28A-D illustrates a series of steps of using the apparatus shown in FIG. 22 to perform an anastomosis according to one implementation.
Figure 28B:
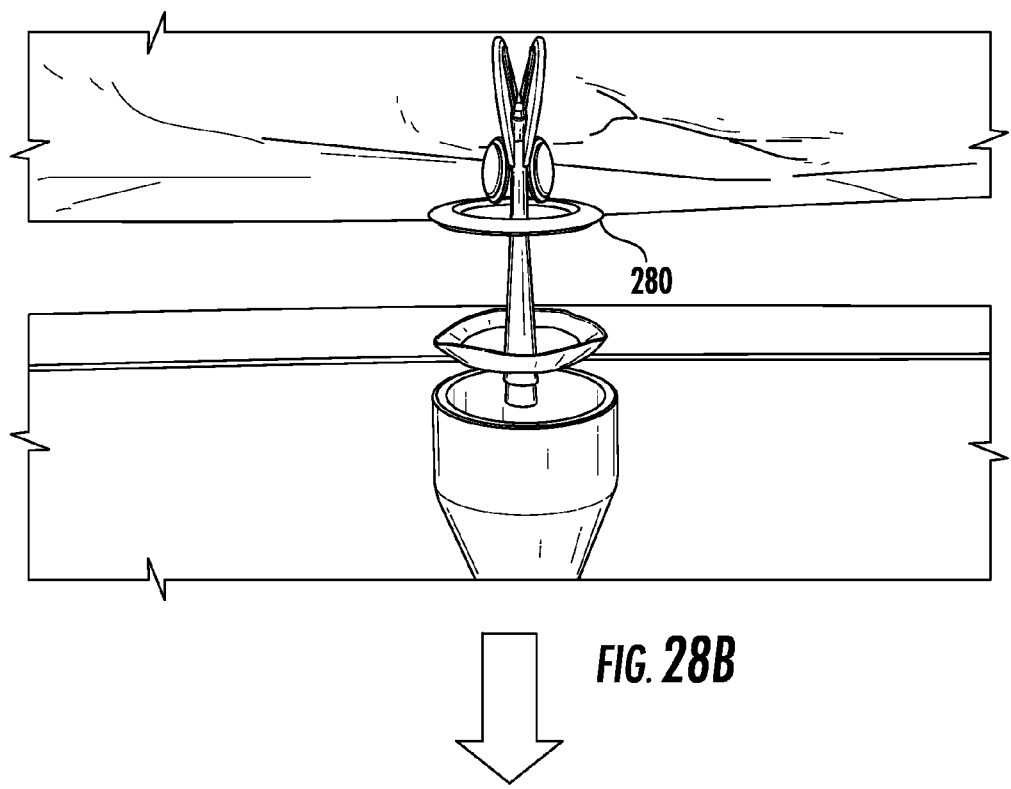
Figure 28C:
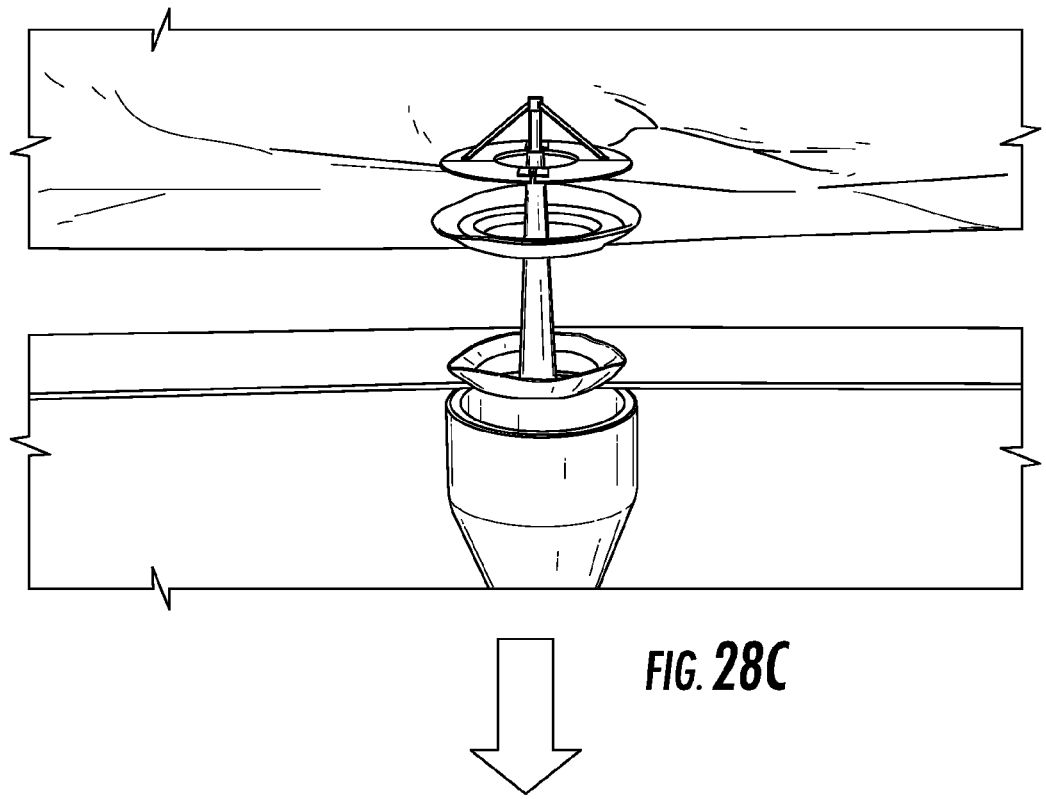
Figure 28D:
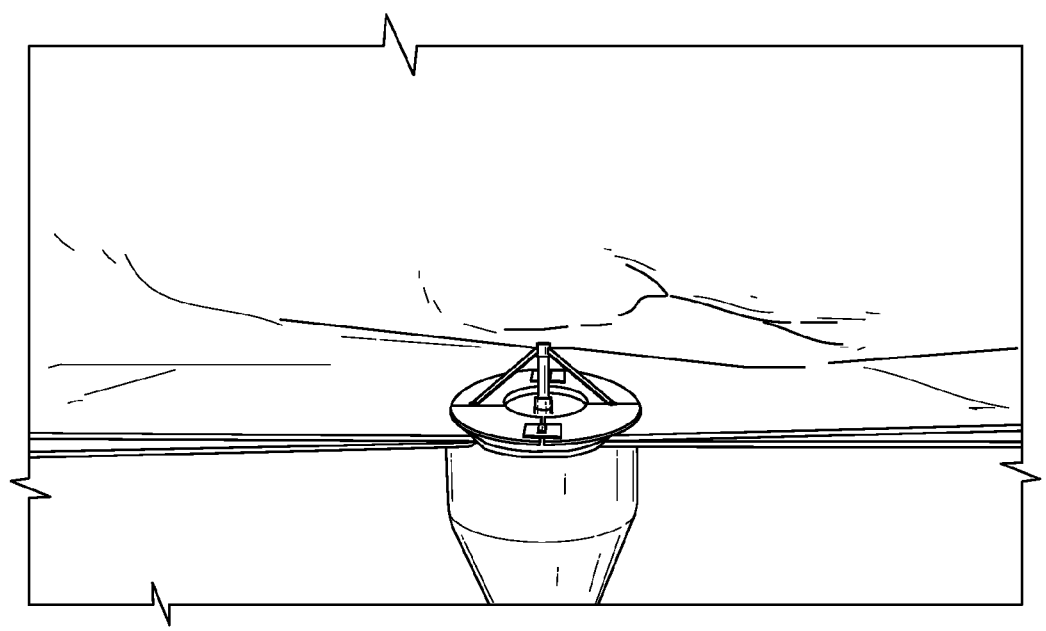

FIGS. 28A-28D illustrate various steps in a method of using the surgical stapling apparatus shown in FIGS. 22-27 according to one implementation. However, it should be understood that the steps described may be used with the other implementations described above in relation to FIGS. 4-21. As shown in FIG. 28A, the anvil assembly 150 and surgical staple dispensing head 12 are inserted into a hole 270 in the body with the anvil plates 56a, 56b in the closed position and the central anvil member 51 in the tilted position. The anvil assembly 150 is then inserted through a second hole 280 in the body, as shown in FIG. 28B. In FIG. 28C, the central anvil member 51 is urged into the transverse position and the anvil plates 56a, 56b are urged into the open position. The anvil plates 56a, 56b and central anvil member 51 are urged toward the surgical staple dispensing head 12 in FIG. 28D. In this position, a plurality of staples may be fired from the surgical staple dispensing head 12 by engaging a lever 98 on the handle 11. After firing the staples, the anvil plates are urged toward the closed position and the central anvil member toward the tilted position, and the anvil assembly and the surgical stapling dispensing head are withdrawn from the holes 270, 280 in the body. Upon withdrawal, the anvil plates may return to the closed position or may be urged to a position between the open and closed positions. In addition, the central anvil member may be returned to the tilted position or to a position between the tilted position and the transverse position.

In the implementations described above, the anvil assemblies are configured to pivot between the tilted and the transverse position. However, alternative implementations may not require tilting between these positions if the footprint of the anvil assembly may be reduced by changing the shape or orientation of the hinged anvil plates or by changing the number of anvil plates.

In addition, in the above described implementations, the first hole 25 of the hinge connector portion 24 is described as being offset from the y-axis and the second hole 27. However, in alternative implementations, the holes 25, 27 may be along the same axis in the tilted position, and translation of the hinge connector portion 24 may be effected by a transverse or arcuate motion of the plunger head or portion thereof.

Furthermore, in alternative implementations, the anvil assembly may have more than two anvil plates, more than one cable, and the cables may extend through the plunger, a portion thereof, or not at all. In addition, alternative actuating mechanisms for translating the plunger upwardly or downwardly and/or for tensioning/releasing tension on the cable may be implemented.

Figure 22:
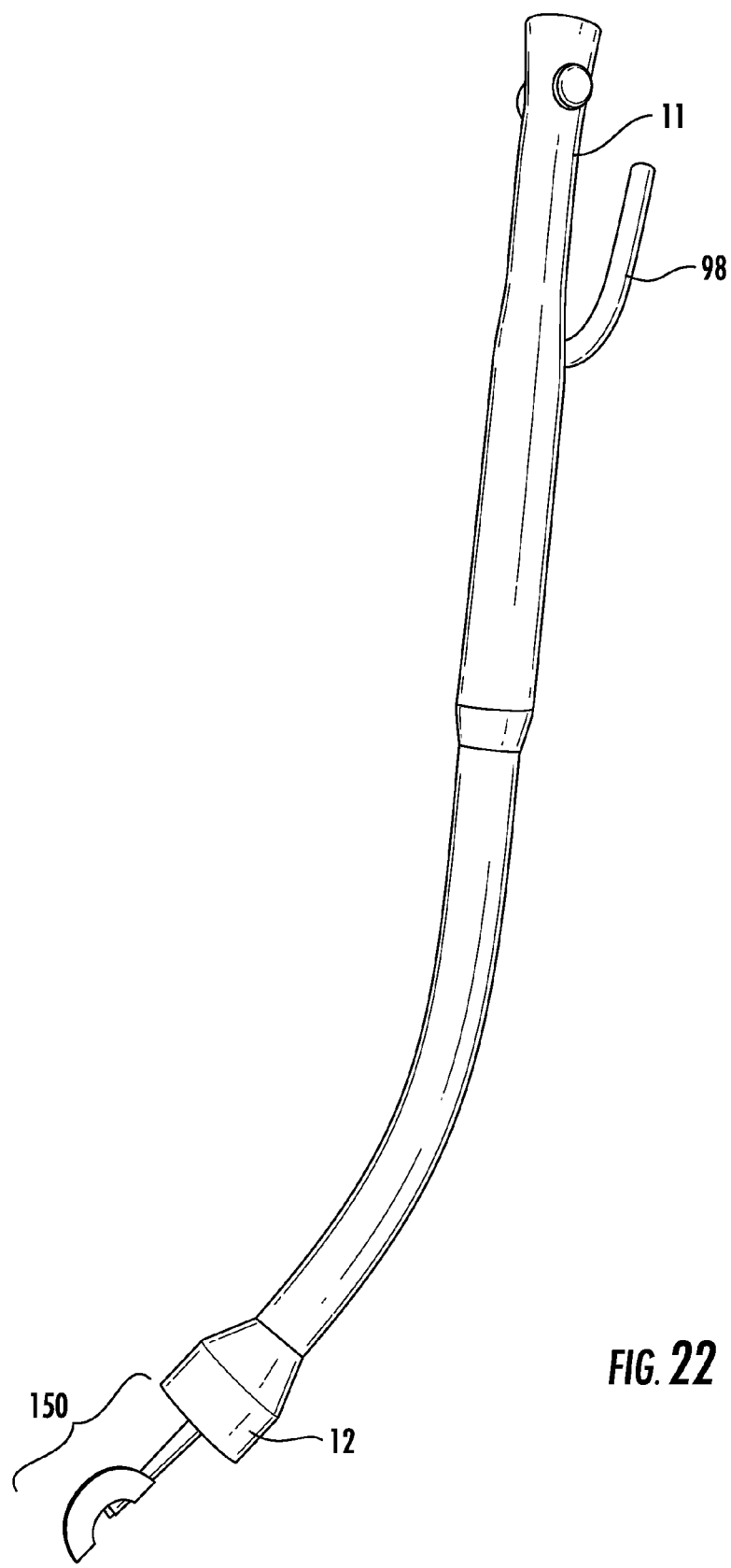
FIG. 22 illustrates a side view of a surgical stapling apparatus according to another implementation.
Figure 23:
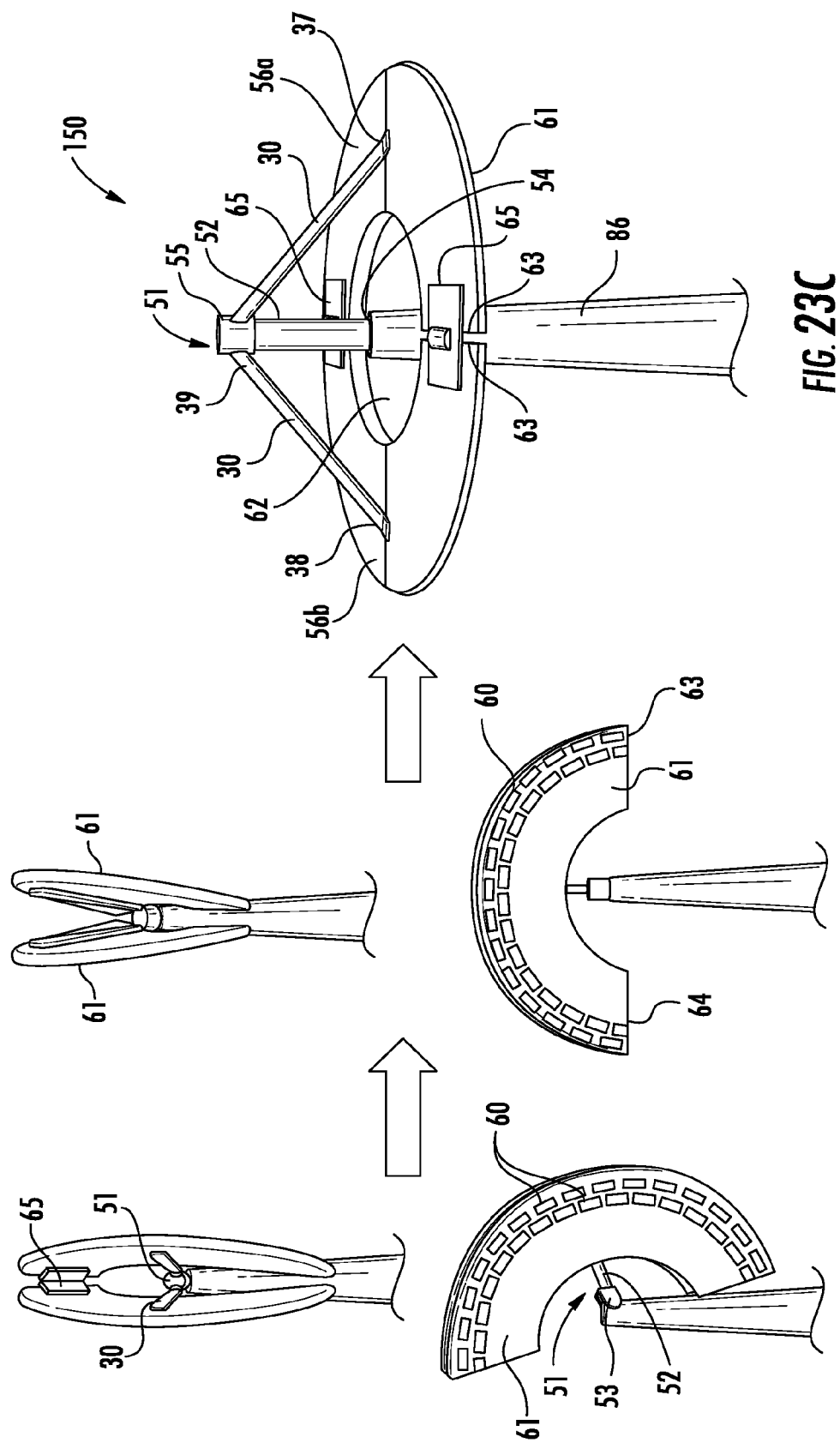
FIG. 23A illustrates front and side views of the anvil assembly of the apparatus shown in FIG. 22 in the tilted and closed positions.
FIG. 23B illustrates the front and side views of the anvil assembly of the apparatus shown in FIG. 22 in the transverse and closed positions.
FIG. 23C illustrates a perspective view of the anvil assembly of the apparatus shown in FIG. 22 in the transverse and open positions.
Figure 24:
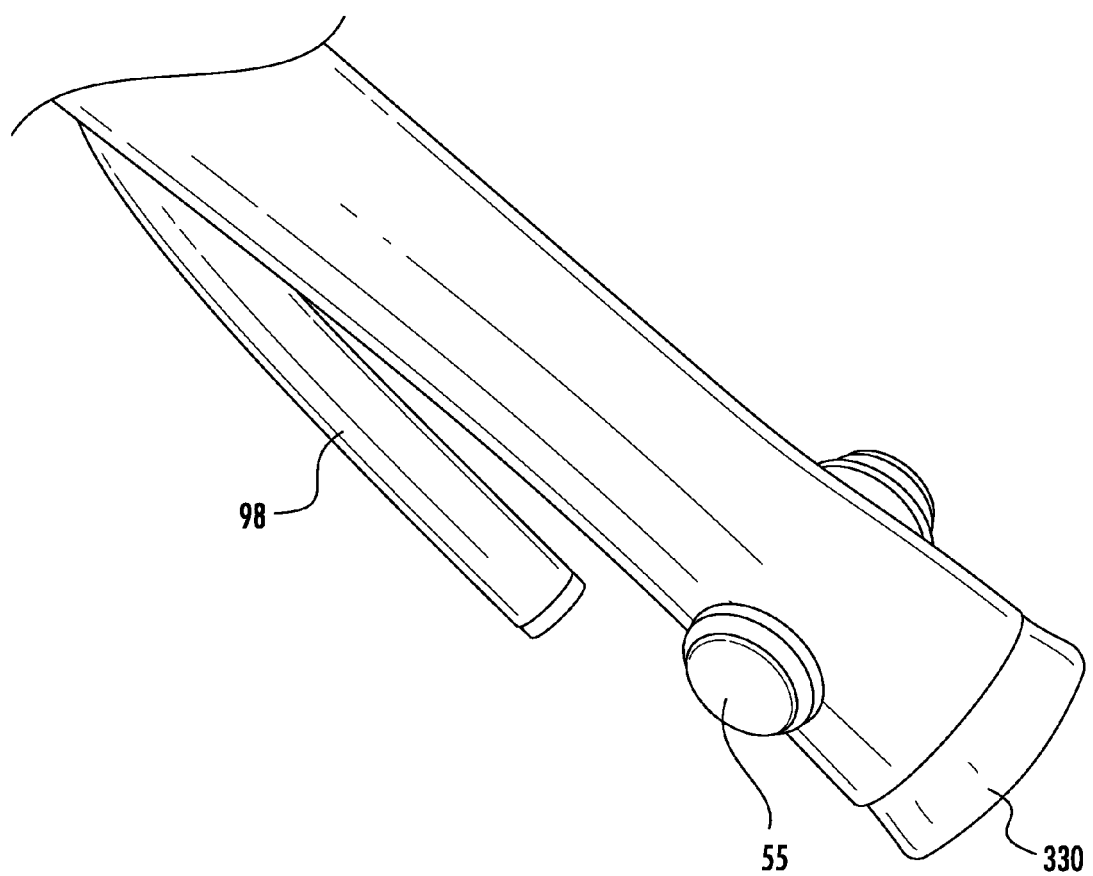
FIG. 24 illustrates a perspective view of a portion of a handle of the apparatus shown in FIG. 22.
Figures 25A, 25B:
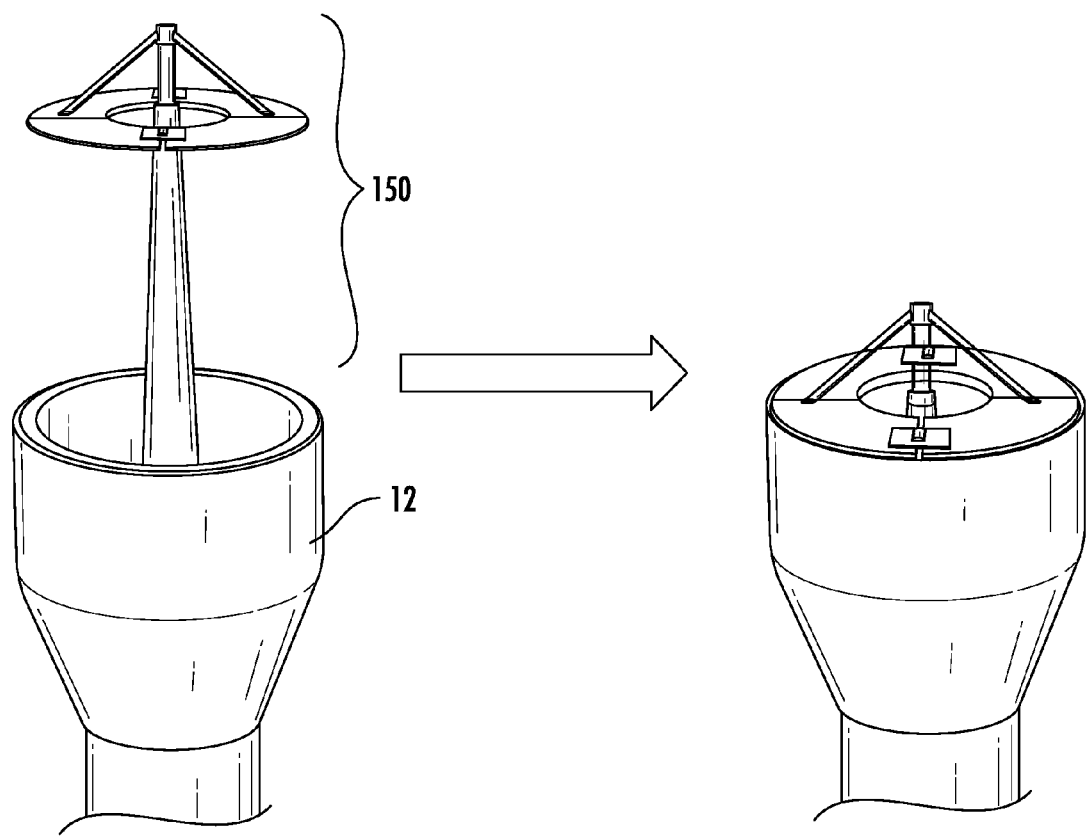
FIG. 25A illustrates a perspective view of the anvil assembly and surgical stapling head of the apparatus shown in FIG. 22 spaced apart.
FIG. 25B illustrates a perspective view of the anvil assembly and surgical stapling head of the apparatus shown in FIG. 22 adjacent each other in preparation for firing the staples against the anvil plates.
Figure 26A:
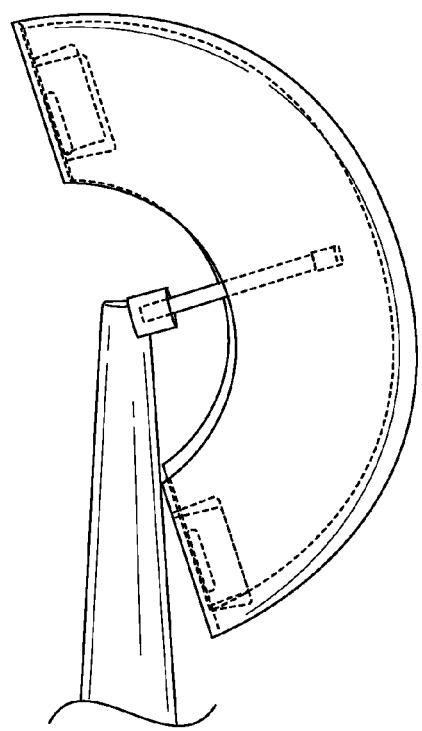
FIG. 26A illustrates a side view of a portion of the anvil assembly of the apparatus shown in FIG. 22 in the tilted and closed positions.
Figure 26B:
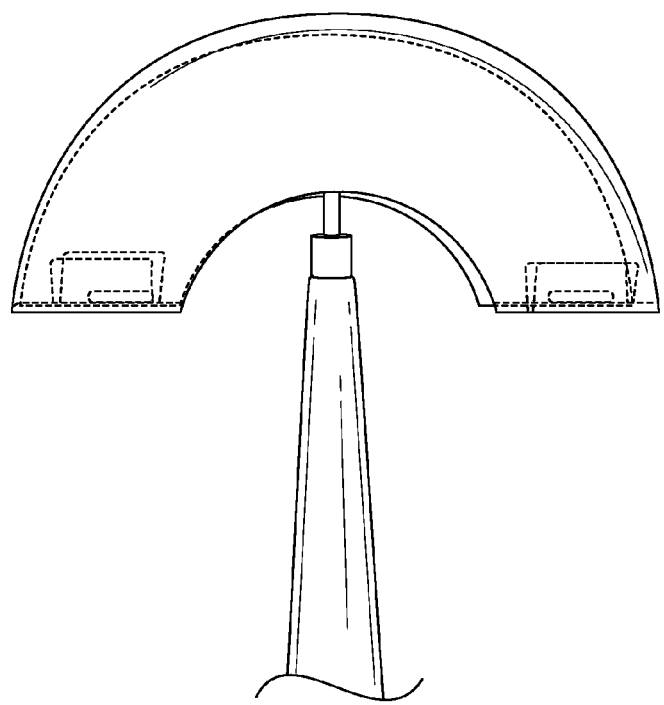
FIG. 26B illustrates a side view of a portion of the anvil assembly of the apparatus shown in FIG. 22 in the transverse and closed positions.
Figure 27A:
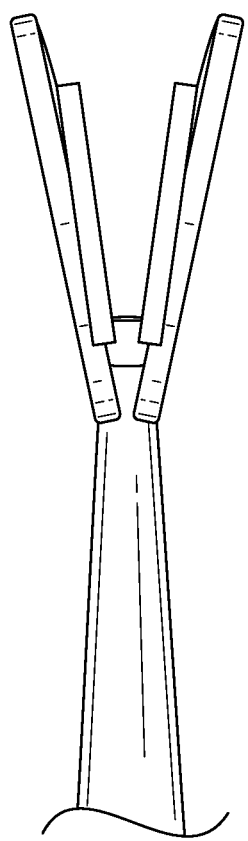
FIG. 27A illustrates a front view of a portion of the anvil assembly of the apparatus shown FIG. 22 in the transverse and closed positions.
Figure 27B:
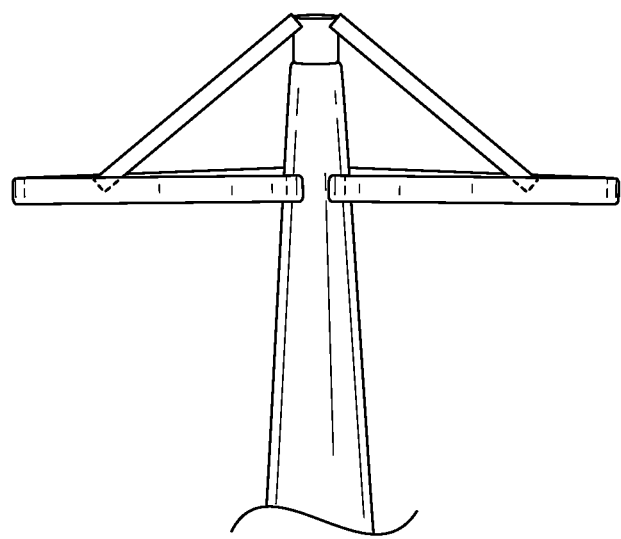
FIG. 27B illustrates a front view of a portion of the anvil assembly of the apparatus shown in FIG. 22 in the transverse and open positions.

In various implementations, mechanisms may be provided in the handle 11 for moving the surgical staple dispensing head 12 and the anvil assembly from an upright position to a bent position as shown in FIG. 22. Because these mechanisms are known in the art, they are not specifically described in this application. Similarly, mechanisms for cutting through tissue and firing staples from the surgical staple dispensing head 12 are known and are not specifically described in this application. For example, U.S. Published Patent Application 2013/0175315 describes such mechanisms and is herein incorporated by reference in its entirety.

In addition, although the implementations described above in relation to FIGS. 4-30 are described as being used in a laparoscopic roux-en-y gastric bypass procedure, it should be understood that the implementations described above may also be used in any procedure requiring an anastomosis between two tissues.

The described methods, systems, and apparatus should not be construed as limiting in any way. Instead, the present disclosure is directed toward all novel and nonobvious features and aspects of the various disclosed implementations, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

The invention claimed is:

1. A surgical stapling apparatus comprising:
a handle;
a surgical staple dispensing head disposed adjacent a distal end of the handle; and
an anvil assembly disposed adjacent a distal end of the surgical staple dispensing head, the anvil assembly comprising:
at least two anvil plates that are separately formed from each other;
a plunger having a proximal end, a distal end, and a central portion there between, the plunger comprising a plunger head at the distal end of the plunger, the plunger being translatable along a y-axis, the y-axis extending from a proximal end of the handle to a distal end of the anvil assembly, and a portion of the central portion of the plunger extends through the surgical staple dispensing head; and
a central anvil member comprising a hinge connector portion that is pivotably connected to the plunger head at a first point and connected to a fixed hinge at a second point, the fixed hinge being separate from the plunger head, and the central anvil member being configured to rotate about the second point between a tilted position and a transverse position, wherein in the tilted position, a distal surface of the central anvil member is not parallel to a transverse plane extending perpendicularly to the y-axis and, in the transverse position, the distal surface of the central anvil member is substantially parallel to the transverse plane,
wherein the first point is offset from the y-axis and the second point is along the y-axis, and the plunger is translatable downwardly along the y-axis for urging the central anvil member to rotate about the second point toward the transverse position and is translatable upwardly along the y-axis for urging the central anvil member to rotate about the second point toward the tilted position.

2. The apparatus of claim 1, further comprising a cable extending between the anvil plates and the central anvil member, the cable being configured for urging the anvil plates between a closed position and an open position, wherein in the open position, the anvil plates are coplanar and, in the closed position, the anvil plates are not coplanar.

3. The apparatus of claim 2, wherein the central anvil member further comprises a generally planar portion, the hinge connector portion extending outwardly from a central portion of a first surface of the generally planar portion, the first surface of the generally planar portion defining a plurality of staple engaging recesses adjacent a portion of a perimeter thereof, and in the transverse position, the first surface of the generally planar portion extends substantially parallel to the transverse plane.

4. The apparatus of claim 3, wherein:
the anvil plates comprise a first anvil plate and a second anvil plate, and
the anvil plates are generally planar, are disposed laterally adjacent the central anvil member, and are hingedly connected to the central anvil member, each plate defining a plurality of staple engaging recesses adjacent a portion of a perimeter thereof on a first surface of each plate, wherein when the anvil plates are in the open position, the first surfaces of the anvil plates and the first surface of the generally planar portion of the central anvil member are substantially parallel to the transverse plane and face toward the surgical staple dispensing head.

5. The apparatus of claim 4, wherein:
the cable has a first end, a second end, and a central portion there between, the first end of the cable being connected to the first anvil plate, the second end of the cable being connected to the second anvil plate, and the central portion of the cable extending through the central anvil member to an actuating mechanism in the handle, and
the actuating mechanism configured for selectively applying and releasing tension on the cable, wherein releasing tension on the cable urges the plates into the closed position and applying tension to the cable urges the plates into the open position.

6. The apparatus of claim 4, wherein the anvil assembly comprises at least one spring loaded hinge assembly, the spring loaded hinge assembly hingedly attaching the central anvil member and each anvil plate, and the spring loaded hinge assembly comprising a hinge spring that is configured for biasing anvil plates toward the closed position.

7. The apparatus of claim 2, wherein the central anvil member comprises a rod, the hinge connector portion extends from a proximal end of the rod, and a portion of the cable extends through the rod adjacent a distal end of the rod to each anvil plate.

8. The apparatus of claim 7, wherein:
the at least two anvil plates comprise a first anvil plate and a second anvil plate, and
the cable has a first end, a second end, and a central portion there between, the first end of the cable being connected to the first anvil plate, the second end of the cable being connected to the second anvil plate, and the central portion of the cable extending through the central anvil member to an actuating mechanism in the handle,
the actuating mechanism configured for selectively applying and releasing tension on the cable, wherein releasing tension on the cable urges the plates into the open position and applying tension to the cable urges the plates into the closed position.

9. The apparatus of claim 7, wherein:
each anvil plate defines a plurality of staple engaging recesses adjacent at least a portion of a perimeter thereof on a first surface of each anvil plate,
the anvil plates are substantially semi-annularly shaped and, in the open position, the first surfaces thereof are disposed in the same plane and together form a generally annular shape, the generally annular shape defining a central hole therethrough, and
the rod of the central anvil member extends through the central hole.

10. The apparatus of claim 9, wherein each of the first and second anvil plates comprise a first end and a second end, and the anvil assembly further comprises a first hinge connecting the first and second anvil plates at the first ends thereof and a second hinge connecting the first and second anvil plates at the second ends thereof.

11. The apparatus of claim 2, wherein the anvil assembly further includes an anvil rod defining an internal channel through which a portion of the plunger and the cable extends, and wherein the fixed hinge is disposed adjacent a distal end of the anvil rod.

12. The apparatus of claim 11, wherein:
the internal channel of the anvil rod defines an annular ledge spaced below the fixed hinge,
the anvil assembly further comprises a compression spring disposed between a proximal end of the plunger head and the annular ledge, and
the compression spring is biased to push the plunger head upwardly from the anvil rod.

13. The apparatus of claim 2, wherein a proximal end of the plunger defines a plurality of indentations to define a rack, and the handle further comprises a rotatable actuating knob that rotates a pinion having teeth that engage the rack, such that rotation of the rotatable actuating knob in a first direction translates the plunger upwardly along the y-axis and rotation of the rotatable actuating knob in a second, opposite direction translates the plunger downwardly along the y-axis.

14. An anvil assembly disposed adjacent a distal end of a surgical staple dispensing head, the anvil assembly comprising:
at least two anvil plates separately formed from each other;
a plunger having a plunger head at a distal end thereof, the plunger being translatable along a y-axis; and
a central anvil member connected to the anvil plates and pivotably connected to the plunger head at a first point and pivotably connected to a fixed hinge at a second point, the fixed hinge being separate from the plunger head, and the central anvil member being configured to rotate about the second point between a tilted position in which a distal surface of the central anvil member is not parallel to a transverse plane extending perpendicularly to the y-axis and a transverse position in which the distal surface of the central anvil member is substantially parallel to the transverse plane, wherein the first point is offset from the y-axis and the second point is along the y-axis, and the plunger is translatable downwardly along the y-axis for urging the central anvil member to rotate about the second point toward the transverse position and is translatable upwardly along the y-axis for urging the central anvil member to rotate about the second point toward the tilted position.

15. The anvil assembly of claim 14, wherein the central anvil member is hingedly connected to the anvil plates.

16. The anvil assembly of claim 14, wherein the central anvil member is connected to the anvil plates by one or more cables.

* * * * *